US008165843B2

(12) United States Patent  
Kimura

(10) Patent No.: US 8,165,843 B2
(45) Date of Patent: Apr. 24, 2012

(54) METHOD AND APPARATUS FOR JUDGING POSITION SHIFT

(75) Inventor: Muneyasu Kimura, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 667 days.

(21) Appl. No.: 12/244,213

(22) Filed: Oct. 2, 2008

(65) Prior Publication Data

US 2009/0099809 A1 Apr. 16, 2009

(30) Foreign Application Priority Data

Oct. 2, 2007 (JP) .................................. 2007-258379

(51) Int. Cl.
*G01P 13/00* (2006.01)
(52) U.S. Cl. ........ 702/150; 702/182; 702/183; 702/189; 702/193; 702/194; 702/199
(58) Field of Classification Search .................. 702/150, 702/182, 183, 189, 193, 194, 199; 703/2
See application file for complete search history.

(56) References Cited

FOREIGN PATENT DOCUMENTS

JP 06-034638 A 2/1994

*Primary Examiner* — Sujoy Kundu
(74) *Attorney, Agent, or Firm* — Sughrue Mion, PLLC

(57) ABSTRACT

Time-course data that has been obtained by measuring, in time series, a change in the density of a sample material by a color reaction thereof is input. A regression curve generation unit generates a regression curve that approximates the time-course data. A standard deviation obtainment unit obtains the value of a standard deviation representing the distribution of the approximation error of the regression curve with respect to the time-course data. A standard deviation comparison judgment unit compares the value of the standard deviation and a predetermined threshold value that is stored in a standard deviation storage unit with each other. When the value of the standard deviation is greater than the threshold value, the standard deviation comparison judgment unit judges that a position shift of the sample material with respect to a sample table is present and outputs the result of the judgment.

16 Claims, 9 Drawing Sheets

METHOD AND APPARATUS FOR JUDGING POSITION SHIFT

BACKGROUND OF THE INVENTION

1. Field of the Invention

The present invention relates to a method and apparatus for judging presence of a position shift of a sample material with respect to a sample table.

2. Description of the Related Art

Conventionally, an apparatus for assaying (quantitatively measuring), based on time-course data, chemical components contained in blood is well known. In the apparatus, blood is dripped into a reaction cell in which a reagent has been deposited, and the reagent and the blood are reacted with each other. Then, time-course data is obtained by measuring, in time series, a change in the density of a sample material that contains the reagent and the blood. As such an apparatus, an apparatus that simultaneously assays a plurality of components, such as glucose and calcium, contained in blood by using reagents, such as a reagent for assaying glucose and a reagent for assaying calcium, respectively is well known. For example, an apparatus in which a plurality of reaction cells are placed on a sample table along the circumference thereof is well known. In the apparatus, sample materials that are different from each other are deposited in the plurality of reaction cells, and these reaction cells are rotated by rotating the sample table. While the reaction cells are rotated, an optical meter that has been fixed to a certain position repeatedly measures a change in the density of each of the sample materials at regular intervals, for example, every eight seconds. Accordingly, time-course data is obtained.

In the apparatus in which a change in the density of a sample material is repeatedly measured while the reaction cells placed along the circumference of the sample table are rotated, as described above, the position of the sample material with respect to the sample table is shifted (incorrectly positioned) in some cases. When a sample material is repeatedly measured, if the position of the sample material is shifted, the accuracy in measurement of a change in the density of the sample material becomes lower. Therefore, obtained time-course data indicates an abnormal value.

As a method for judging the abnormality of the time-course data, a method in which it is expected that the density of the sample material will not reach a predetermined density within a predetermined time period, it is judged that the time-course data is abnormal is well known. In this method, if the time-course data is judged to be abnormal, the measurement is stopped before completion, and measurement is carried out again (please refer to Japanese Unexamined Patent Publication No. 6 (1994)-034638).

In the apparatus that measures each of a plurality of sample materials in time series by repeatedly conveying each of the plurality of sample materials to a measurement position by movement of a sample table on which the plurality of sample materials are placed, abnormality of time-course data is caused by a shift in the position of a sample material with respect to the sample table in most cases. Therefore, presence of a position shift of a sample material with respect to the sample table (in other words, whether the position of a sample material is shifted with respect to the position of the sample table) may be judged by judging whether the time-course data is abnormal or not.

However, the fluctuation of the time-course data that is caused by the shift in the position of the sample material with respect to the sample table has various kinds of patterns. Therefore, if the abnormality of the time-course data is judged only based on whether the density of a sample material has reached a predetermined density within a predetermined time period, abnormality is not detected in some cases. Hence, it is impossible to accurately distinguish normal time-course data and abnormal time-course data from each other in some cases. Specifically, it is impossible to accurately judge presence of a shift in the position of a sample material with respect to the sample table by using the time-course data in some cases.

SUMMARY OF THE INVENTION

In view of the foregoing circumstances, it is an object of the present invention to provide a method and apparatus for judging a position shift that can improve the reliability of judgment on presence of a position shift of a sample material with respect to a sample table.

A first method for judging a position shift according to the present invention is a method for judging a position shift, wherein when each of a plurality of sample materials is measured in time series by repeatedly conveying each of the plurality of sample materials to a measurement position by moving a sample table, on which the plurality of sample materials are placed, presence of a position shift of each of the plurality of sample materials with respect to the sample table is judged, and wherein when the value of a standard deviation representing the distribution of the approximation error of a regression curve that approximates the values of time-course data obtained by measuring, in time series, a change in the density of the sample material by a color reaction thereof is greater than a predetermined threshold value, it is judged that a position shift of the sample material with respect to the sample table is present.

A second method for judging a position shift according to the present invention is a method for judging a position shift, wherein when each of a plurality of sample materials is measured in time series by repeatedly conveying each of the plurality of sample materials to a measurement position by moving a sample table, on which the plurality of sample materials are placed, presence of a position shift of each of the plurality of sample materials with respect to the sample table is judged, and wherein when time-course data is obtained by measuring, in time series, a change in the density of each of the plurality of sample materials by a color reaction thereof, if the ratio of a time period in which the value of the time-course data is increasing or a time period in which the value of the time-course data is decreasing with respect to the total time period in which the time-course data is being obtained deviates from a predetermined range of values, it is judged that a position shift of the sample material with respect to the sample table is present.

A first apparatus for judging a position shift according to the present invention is an apparatus for judging a position shift, wherein when each of a plurality of sample materials is measured in time series by repeatedly conveying each of the plurality of sample materials to a measurement position by moving a sample table, on which the plurality of sample materials are placed, presence of a position shift of each of the plurality of sample materials with respect to the sample table is judged, the apparatus comprising:

a regression curve generation means for generating a regression curve that approximates time-course data obtained by measuring, in time series, a change in the density of each of the plurality of sample materials by a color reaction thereof;

a standard deviation obtainment means for obtaining the value of a standard deviation representing the distribution of the approximation error of the regression curve; and a standard deviation comparison judgment means for comparing the value of the standard deviation and a predetermined threshold value with each other, wherein when the value of the standard deviation is greater than the threshold value, the standard deviation comparison judgment means judges that a position shift of the sample material with respect to the sample table is present and outputs the result of the judgment.

A second apparatus for judging a position shift according to the present invention is an apparatus for judging a position shift, wherein when each of a plurality of sample materials is measured in time series by repeatedly conveying each of the plurality of sample materials to a measurement position by moving a sample table, on which the plurality of sample materials are placed, presence of a position shift of each of the plurality of sample materials with respect to the sample table is judged, the apparatus comprising:

a time ratio obtainment means for obtaining the ratio of a time period in which the value of time-course data is increasing or a time period in which the value of the time-course data is decreasing with respect to the total time period in which the time-course data is being obtained, the time-course data being obtained by measuring, in time series, a change in the density of each of the plurality of sample materials by a color reaction thereof; and a time ratio comparison judgment means for comparing the ratio and a predetermined range of values with each other, wherein when the ratio deviates from the predetermined range of values, the time ratio comparison judgment means judges that a position shift of the sample material with respect to the sample table is present and outputs the result of the judgment.

The second apparatus for judging a position shift may further include:

a regression curve generation means for generating a regression curve that approximates the time-course data;

a standard deviation obtainment means for obtaining the value of a standard deviation representing the distribution of the approximation error of the regression curve with respect to the time-course data; and a standard deviation comparison judgment means for comparing the value of the standard deviation and a predetermined threshold value with each other, wherein when the value of the standard deviation is greater than the threshold value, the standard deviation comparison judgment means judges that a position shift of the sample material with respect to the sample table is present and outputs the result of the judgment.

The apparatus for judging a position shift may further include:

an increase/decrease obtainment means for obtaining the number of times of increase/decrease of the values of the time-course data and the order of increase/decrease thereof; and an increase/decrease comparison judgment means for comparing the obtained number of times of increase/decrease and the obtained order of increase/decrease with a predetermined number of times of increase/decrease and a predetermined order of increase/decrease, respectively, wherein when at least one of the obtained number of times of increase/decrease and the obtained order of increase/decrease differs from the predetermined number of times of increase/decrease and the predetermined order of increase/decrease, respectively, the increase/decrease comparison judgment means judges that a position shift of the sample material with respect to the sample table is present and outputs the result of the judgment.

The predetermined number of times of increase/decrease may be a plurality of kinds of numbers, which are different from each other.

The number of times of increase/decrease is the total of the number of times of increase of the value of the time-course data in time series and the number of times of decrease of the value of the time-course data in time series.

Further, the order of increase/decrease represents the order of increase/decrease of the values of the time-course data. The order of increase/decrease defines whether the fluctuation pattern of the time-course data starts with an increase or a decrease in the value of the time-course data.

The apparatus for judging a position shift may further include:

a power ratio obtainment means for obtaining the ratio of the power of a power spectrum in a frequency range that is higher than or equal to a predetermined frequency with respect to the total power of the power spectrum, the power spectrum being obtained by performing Fourier transformation on the time-course data; and a power ratio comparison judgment means for comparing the ratio and a predetermined threshold value with each other, wherein when the ratio is higher than the predetermined threshold value, the power ratio comparison judgment means judges that a position shift of the sample material with respect to the sample table is present and outputs the result of the judgment.

Further, the time-course data may be a moving average of the values obtained by measuring, in time series, a change in the density of each of the plurality of sample materials by a color reaction thereof.

The inventor of the present invention has focused on a characteristic feature of time-course data obtained by accurately (correctly) measuring a change in the density of a sample material by a color reaction thereof. The accurately-measured time-course data fluctuates along a smooth curve, such as a monotonously-increasing curve, a monotonously-decreasing curve, a convex curve that monotonously increases first and monotonously decreases after the increase and a concave curve that monotonously decreases first and monotonously increases after the decrease, which has small fluctuation. The inventor of the present invention has found that presence of a position shift of the sample material with respect to the sample table can be more accurately judged by using the aforementioned characteristic of the time-course data, and reached the present invention based on the finding.

According to a first method and apparatus for judging a position shift of the present invention, when the value of a standard deviation representing the distribution of the approximation error of a regression curve that approximates the time-course data is greater than a predetermined threshold value, it is judged that the time-course data is abnormal. Therefore, it is possible to improve the reliability of the judgment on presence of a position shift of the sample material with respect to the sample table.

Specifically, the fluctuation pattern of accurately-measured time-course data is a smooth fluctuation pattern that has small fluctuation. Therefore, it is possible to reduce the approximation error of a regression curve by regressing the data by a function (for example, a quadratic function or the like) that represents a smooth curve. In contrast, the fluctuation pattern of abnormal time-course data, which has not been measured accurately, in other words, which has been measured when a position shift of the sample material with respect to the sample table is present, includes many fluctuation components. Therefore, the abnormal time-course data does not fluctuate along a smooth curve. Hence, the magnitude and the variance of the approximation error of the abnormal data approximated by the regression function become large.

Therefore, it is possible to distinguish the value of a standard deviation representing the distribution of approximation error obtained for normal time-course data and the value of a standard deviation representing the distribution of approximation error obtained for abnormal time-course data from each other. Further, it is possible to set, in advance, a threshold value for distinguishing the two values, in other words, a threshold value for the value of the standard deviation. Accordingly, when a standard deviation obtained for time-course data exceeds the predetermined threshold value, it is possible to judge that the time-course data is abnormal. In other words, it is possible to judge that a position shift of the sample material with respect to the sample table is present. Therefore, it is possible to reduce the risk of overlooking the abnormality of the time-course data than the conventional method. Hence, it is possible to improve the reliability of the judgment on the presence of a position shift of the sample material with respect to the sample table.

According to a second method and apparatus for judging a position shift of the present invention, when the ratio of a time period in which the value of the time-course data is increasing or a time period in which the value of the time-course data is decreasing with respect to the total time period in which the time-course data is being obtained deviates from a predetermined range of ratios, it is judged that the time-course data is abnormal. Therefore, it is possible to improve the reliability of the judgment on presence of a position shift of the sample material with respect to the sample table.

Specifically, the fluctuation pattern of accurately-measured time-course data is a smooth fluctuation pattern that has small fluctuation. The accurately-measured time-course data is stable and fluctuates along a smooth fluctuation curve, such as a monotonously-increasing curve, a monotonously-decreasing curve, a curve that monotonously increases first and monotonously decreases only once after the increase and a curve that monotonously decreases first and monotonously increases only once after the decrease. Therefore, the ratio (hereinafter, also referred to as a time ratio) of a time period in which the value of the density of the sample material is increasing or a time period in which the value of the density is decreasing with respect to the total time period in which the time-course data is being obtained falls within a certain range. In contrast, the fluctuation pattern of abnormal time-course data includes many fluctuation components and is not stable. Therefore, the time ratio for the abnormal time-course data does not fall within a certain range in many cases.

Therefore, it is possible to distinguish the time ratio for the normal time-course data, which falls within the certain range, and the time ratio for the abnormal time-course data, which does not fall within the certain range, from each other. Further, it is possible to set, in advance, a range of time ratios for distinguishing the normal time-course data and the abnormal time-course data from each other. Accordingly, when the time ratio of input time-course data deviates from a predetermined range of time ratios, it is possible to judge that the time-course data is abnormal. Therefore, it is possible to reduce the risk of overlooking the abnormality of the time-course data than the conventional method. Hence, it is possible to improve the reliability of the judgment on the presence of a position shift of the sample material with respect to the sample table.

Further, the first method for judging a position shift and the second method for judging a position shift may be combined with each other. Specifically, when the time-course data is judged to be abnormal by at least one of the first method for judging a position shift and the second method for judging a position shift, it is judged that the time-course data is abnormal. If the two methods are used in combination, it is possible to improve the reliability of the judgment on the presence of a position shift of the sample material with respect to the sample table.

Further, the apparatus for judging a position shift may further include an increase/decrease obtainment means for obtaining the number of times of increase/decrease of the values of the time-course data and the order of increase/decrease thereof, and an increase/decrease comparison judgment means for comparing the obtained number of times of increase/decrease and the obtained order of increase/decrease with a predetermined number of times of increase/decrease and a predetermined order of increase/decrease, respectively. Further, when at least one of the obtained number of times of increase/decrease and the obtained order of increase/decrease differs from the predetermined number of times of increase/decrease and the predetermined order of increase/decrease, respectively, the increase/decrease comparison judgment means may also judge that a position shift of the sample material with respect to the sample table is present and output the result of the judgment. If the increase/decrease obtainment means and the increase/decrease comparison judgment means are further provided, it is possible to improve the reliability of the judgment on the presence of a position shift of the sample material with respect to the sample table.

Specifically, the fluctuation pattern of accurately-measured time-course data is a smooth fluctuation pattern that has small fluctuation. The accurately-measured time-course data fluctuates along a smooth fluctuation curve, such as a monotonously-increasing curve, a monotonously-decreasing curve, a curve that monotonously increases first and monotonously decreases only once after the increase and a curve that monotonously decreases first and monotonously increases only once after the decrease. Therefore, the number of times of increase/decrease of the value of the time-course data and the order of increase/decrease fall within certain ranges. In contrast, the fluctuation pattern of abnormal time-course data includes many fluctuation components, and the cycle and the order of increase/decrease are not stable. Therefore, the number of times of increase/decrease and the order of increase/decrease do not fall within certain ranges in many cases.

Therefore, it is possible to distinguish the number of times of increase/decrease and the order of increase/decrease for the normal time-course data, which fall within the certain ranges, and the number of times of increase/decrease and the order of increase/decrease for the abnormal time-course data, which do not fall within the certain ranges, from each other. Further, it is possible to set the number of times of increase/decrease and the order of increase/decrease in advance to distinguish the numbers of times of increase/decrease and the orders of increase/decrease between the normal time-course data and the abnormal time-course data. Accordingly, when at least one of the number of times of increase/decrease and the order of increase/decrease of the input time-course data differs from the predetermined number of times of increase/decrease and the predetermined order of increase/decrease, respectively, it is possible to judge that the time-course data is abnormal. Therefore, it is possible to reduce the risk of overlooking the abnormality of the time-course data than the conventional method. Hence, it is possible to further improve the reliability of the judgment on the presence of a position shift of the sample material with respect to the sample table.

Further, the apparatus for judging a position shift may further include a power ratio obtainment means for obtaining the ratio of the power of a power spectrum in a frequency range that is higher than or equal to a predetermined frequency with respect to the total power of the power spectrum, the power spectrum being obtained by performing Fourier transformation on the time-course data, and a power ratio comparison judgment means for comparing the ratio and a predetermined threshold value with each other. Further, when the ratio is higher than the predetermined threshold value, the power ratio comparison judgment means may also judge that a position shift of the sample material with respect to the sample table is present and output the result of the judgment. If the power ratio obtainment means and the power ratio comparison judgment means are further provided, it is possible to further improve the reliability of the judgment on the presence of a position shift of the sample material with respect to the sample table.

Specifically, the fluctuation pattern of accurately-measured time-course data is a smooth pattern that has a small fluctuation. Therefore, in a power spectrum obtained by Fourier transformation on the accurately-measured time-course data, the power of the power spectrum on the low-frequency side is high, and that of the spectrum on the high-frequency side is low. In contrast, the fluctuation pattern of abnormal time-course data is not a smooth pattern, because the abnormal time-course data includes many fluctuation components. Further, the cycle of fluctuation tends to be short. Therefore, in a power spectrum obtained by performing Fourier transformation on the abnormal time-course data, the power of the power spectrum on the high-frequency side is high, compared with the normal time-course data.

Therefore, it is possible to distinguish the power spectrum for the normal time-course data and the power spectrum for the abnormal time-course data. Further, it is possible to set a threshold value that can more accurately distinguish the two power spectra by appropriately determining a predetermined frequency for obtaining the power ratio, in other words, it is possible to set a threshold value for the power ratio. Accordingly, when the power ratio for the input time-course data is higher than the predetermined threshold value, it is possible to identify that the time-course data is abnormal. Therefore, it is possible to further reduce the risk of overlooking the abnormality of the time-course data than the conventional method. Hence, it is possible to improve the reliability of the judgment on the presence of a position shift of the sample material with respect to the sample table.

If the time-course data is a moving average of the values obtained by measuring, in time series, a change in the density of a sample material by a color reaction thereof, it is possible to further improve the reliability of the judgment on the presence of a position shift of the sample material with respect to the sample table. Specifically, the moving average of the time-course data is obtained to remove subtle noise before other processing. Accordingly, it is possible to further improve the reliability of the judgment on the presence of a position shift of the sample material with respect to the sample table.

DETAILED DESCRIPTION OF THE INVENTION

Figure 1:
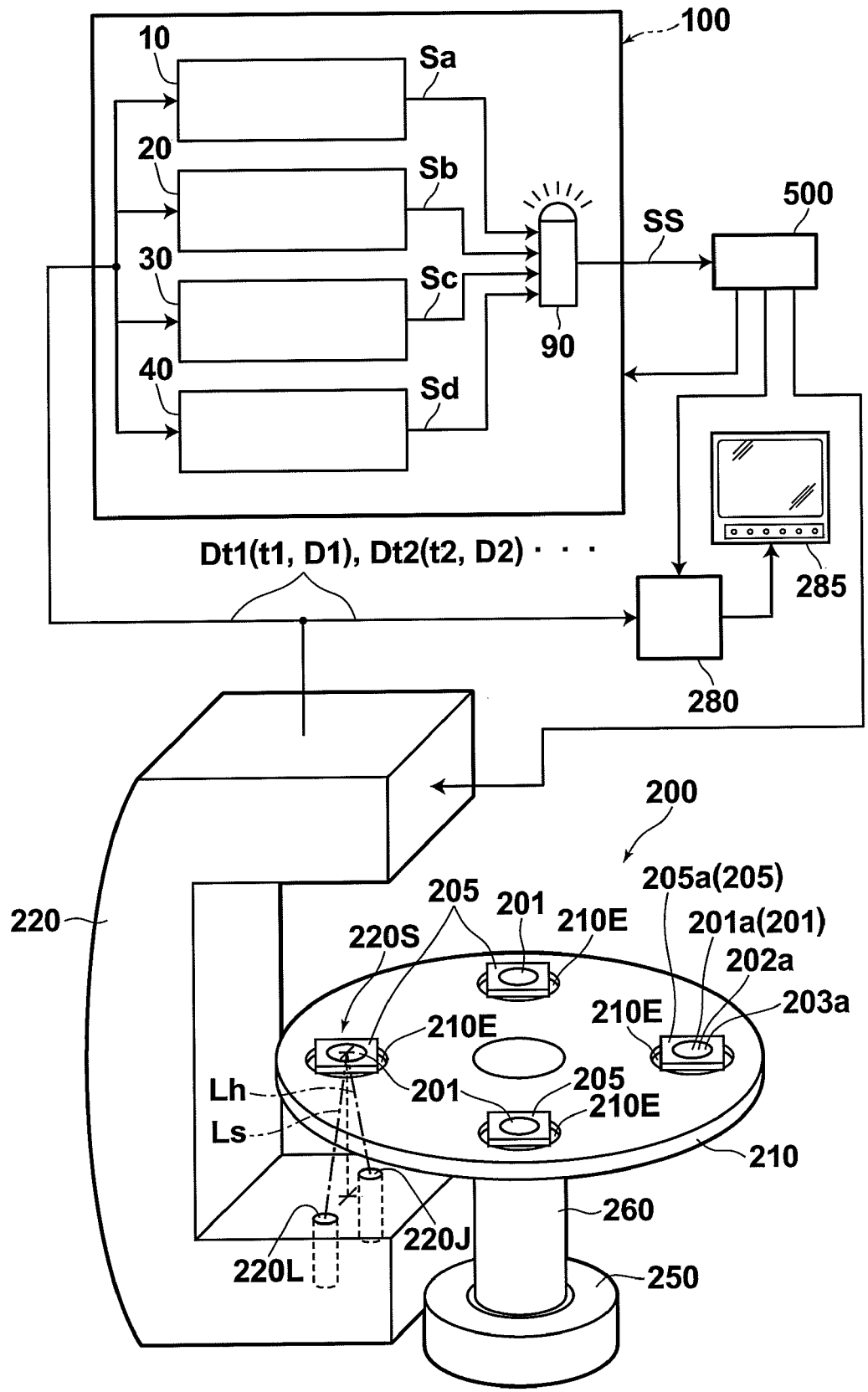
FIG. 1 is a conceptual diagram schematically illustrating the configuration of a position shift judgment apparatus and a time-course data measurement apparatus.
Figure 2:
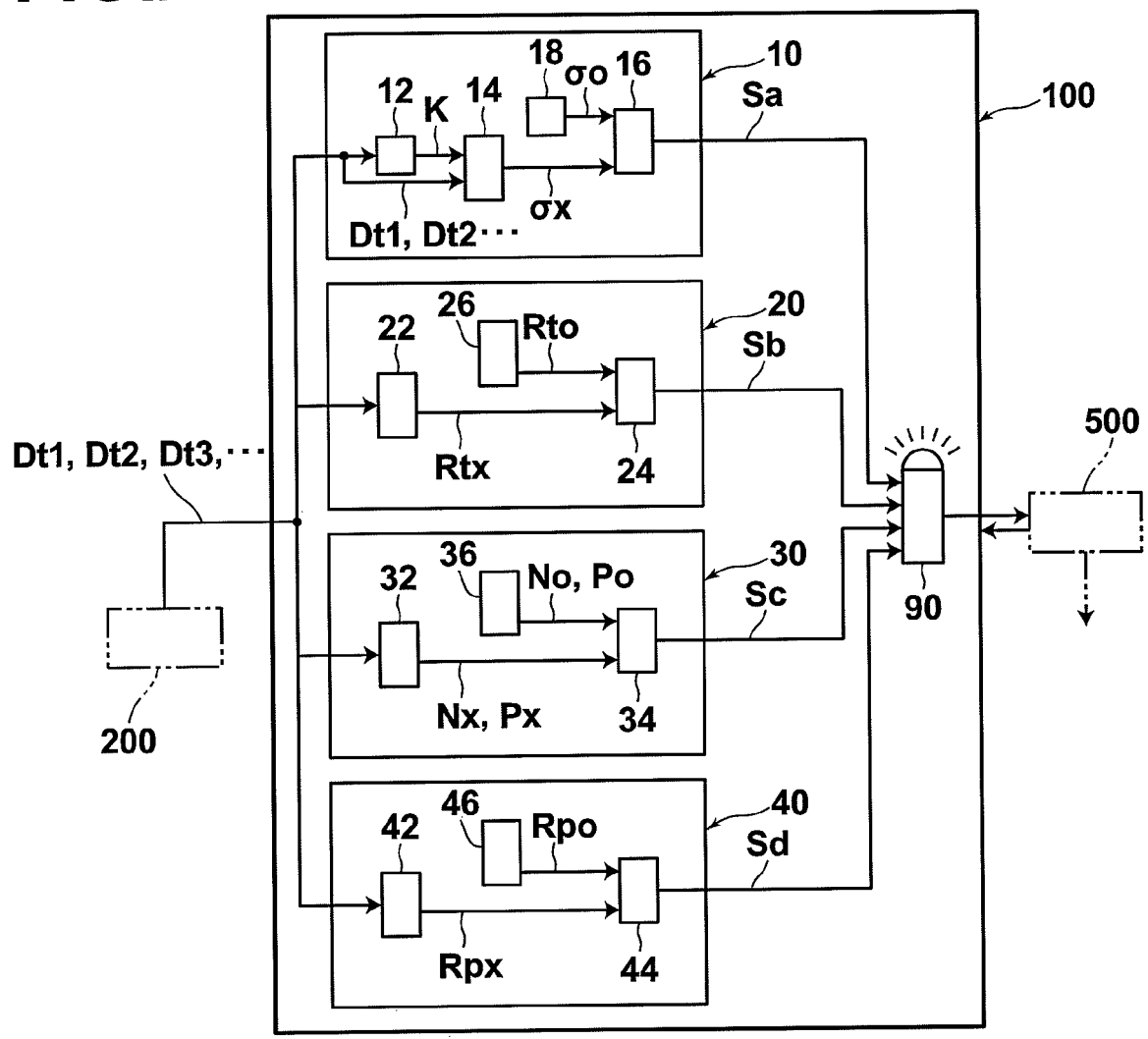
FIG. 2 is a block diagram illustrating the configuration of the position shift judgment apparatus.

Hereinafter, embodiments of the present invention will be described with reference to drawings. FIG. 1 is a conceptual diagram schematically illustrating the configuration of a position shift judgment apparatus and a time-course data measurement apparatus. The position shift judgment apparatus judges by using a method for judging a position shift according to the present invention, and the time-course data measurement apparatus measures time-course data. FIG. 2 is a block diagram illustrating the configuration of the position shift judgment apparatus that uses the method for judging a position shift, in detail.

A position shift judgment apparatus 100, illustrated in FIGS. 1 and 2, judges presence of a shift in the position of a sample material with respect to a sample table by judging the abnormality of time-course data (whether the time-course data is abnormal). The time-course data is obtained by measuring, in time series, a change in the density of the sample material by a color reaction thereof. The measurement of the time-course data is carried out by a time-course data measurement apparatus 200.

The time-course data measurement apparatus 200 obtains values D1, D2, D3, . . . , which represent the densities of a sample material 201 at time t1, t2, t3, . . . , respectively. The values D1, D2, D3, . . . are obtained by measuring, in time series, a change in the density of a sample material 201 by a color reaction thereof, and the sample material 201 includes a reagent deposited in a reaction cell 205 and blood dripped onto the reagent. The reaction cell 205 is placed on a rotary disk 210, which is a sample table, and provided for measurement. Here, data representing value D1 of density at time t1 is referred to as time-course data Dt1 (t1, D1). Data representing value D2 at time t2 is referred to as time-course data Dt2 (t2, D2). Data representing value D3 at time t3 is referred to as time-course data Dt3 (t3, D3).

The time-course data after the time-course data Dt3 is referred to in a similar manner. Hereinafter, time-course data Dt1 (t1, D1), Dt2 (t2, D2), Dt3 (t3, D3), . . . are simply referred to as time-course data Dt1, Dt2, Dt3, . . . .

The operation of the whole measurement system including the position shift judgment apparatus 100, the time-course data measurement apparatus 200 and the like and the timing of the operation are controlled by a controller 500.

Further, as the time-course data Dt1, Dt2, Dt3, . . . , a moving average of the time-course data, which is obtained by performing a moving average operation on the time-course data obtained by the time-course data measurement apparatus 200, may be used. The operation for obtaining the moving average of the time-course data may be performed on the time-course data measurement apparatus 200 side or on the position shift judgment apparatus 100 side. For example, when the operation for obtaining the moving average is performed on the position shift judgment apparatus 100 side, a regression curve generation unit 12, a time ratio obtainment unit 22, an increase/decrease obtainment unit 32, a power ratio obtainment unit 42 and the like, which will be described later, may generate a regression curve and obtain a time ratio after obtaining a moving average of the time-course data by performing a moving average operation on the time-course data.

The position shift judgment apparatus 100 includes a first abnormality judgment unit 10, which includes a regression curve generation unit 12, a standard deviation obtainment unit 14, a standard deviation comparison judgment unit 16 and a standard deviation storage unit 18. The regression curve generation unit 12 generates regression curve K that is represented by a quadratic function for example. The regression curve K approximates time-course data Dt1, Dt2, Dt3, . . . , which is received from the time-course data measurement apparatus 200. The standard deviation obtainment unit 14 obtains standard-deviation value σx, which represents the deviation (distribution) of the approximation error of the regression curve K, to which the time-course data Dt1, Dt2, Dt3, . . . are approximated, with respect to the time-course data Dt1, Dt2, Dt3, . . . . The standard deviation comparison judgment unit 16 compares the standard-deviation value σx and a predetermined threshold value σo with each other. When the standard-deviation value σx is greater than the predetermined threshold value σo, the standard deviation comparison judgment unit 16 judges that the time-course data Dt1, Dt2, Dt3, . . . is abnormal, and outputs the result of the judgment. The standard deviation storage unit 18 stores the predetermined threshold value σo.

In the first abnormality judgment unit 10, it is not necessary that the time-course data is regressed by a quadratic function. The time-course data may be regressed by any kind of function that represents a smooth curve that has a small fluctuation.

The standard deviation obtainment unit 14 obtains approximation errors ∈t1, ∈t2, ∈t3, . . . of the regression curve K with respect to the time-course data Dt1, Dt2, Dt3, . . . . Further, the standard deviation obtainment unit 14 obtains the standard deviation value ax of the approximation errors ∈t1, ∈t2, ∈t3, The threshold value σo, which is stored in advance in the standard deviation storage memory 18, is determined so that normal time-course data, which is obtained when measurement is performed normally, and abnormal time-course data, which is obtained when measurement is not performed normally, can be distinguished from each other.

Specifically, it has been known that normal time-course data can accurately approximate to a smooth curve, such as a quadratic curve, that has a small fluctuation. Therefore, the standard deviation value of approximation errors of a regression curve with respect to normal time-course data, the regression curve regressing the normal time-course data, seldom exceeds a predetermined value. Hence, the predetermined value may be determined as the threshold value σo.

The threshold value σo, which has been determined as described above, is input to the standard deviation storage unit 18 and stored therein.

The standard deviation comparison judgment unit 16 compares the standard deviation value σx, which is received from the standard deviation obtainment unit 14, and the threshold value σo, which is stored in the storage unit 18, with each other. The standard deviation value σx is the standard deviation of approximation errors of a regression curve with respect to the time-course data Dt1, Dt2, Dt3, . . . , the regression curve regressing the time-course data Dt1, Dt2, Dt3, . . . . When the standard deviation value σx is greater than the threshold value ao, the standard deviation comparison judgment unit 16 judges that the time-course data is abnormal. In other words, it is judged that the position of the sample material 201 is shifted with respect to the rotary disk 210 (sample table). Then, signal Sa indicating that a position shift is present is output.

Here, when the standard deviation value σx does not exceed the threshold value σo, the standard deviation comparison judgment unit 16 does not judge that the time-course data is abnormal. In other words, it is not judged that the position of the sample material 201 is shifted with respect to the rotary disk 210 (sample table). Therefore, signal Sa indicating that a position shift is present is not output.

The position shift judgment apparatus 100 includes an alarm (a warning device) 90. The signal Sa that has been output from the standard deviation comparison judgment unit 16 is input to the alarm 90, and the alarm 90 warns that the position of the sample material is shifted with respect to the sample table by voice (sound) or by displaying information on a screen.

Further, the position shift judgment apparatus 100 includes a second abnormality judgment unit 20, a third abnormality judgment unit 30 and a fourth abnormality judgment unit 40 in addition to the first abnormality judgment unit 10.

The second abnormality judgment unit 20 includes a time ratio obtainment unit 22, a time ratio comparison judgment unit 24, a time ratio storage unit 26 and the like, which are elements for judging presence of a position shift of the sample material 201 with respect to the rotary disk 210 (sample table) and for outputting the result of the judgment. The position shift of the sample material 201 is judged by judging the abnormality of time-course data based on the ratio of a time period in which the value of the time-course data is increasing or a time period in which the value of the time-course data is decreasing with respect to the total time period in which the time-course data is being obtained.

The third abnormality judgment unit 30 includes an increase/decrease obtainment unit 32, an increase/decrease comparison judgment unit 34, an increase/decrease storage unit 36, and the like, which are elements for judging presence of a position shift of the sample material 201 with respect to the rotary disk 210 (sample table) and for outputting the result of the judgment. The position shift of the sample material 201 is judged by judging the abnormality of time-course data based on the number of times of increase/decrease of the value of the time-course data and the order of increase/decrease thereof.

The fourth abnormality judgment unit 40 includes a power ratio obtainment unit 42, a power ratio comparison judgment unit 44, a power ratio storage unit 46, and the like, which are elements for judging presence of a position shift of the sample material 201 with respect to the rotary disk 210 (sample table) and for outputting the result of the judgment. The position shift of the sample material 201 is judged by judging the abnormality of time-course data based on a power spectrum obtained by performing Fourier transformation on the time-course data.

Next, the second abnormality judgment unit 20, the third abnormality judgment unit 30, and the fourth abnormality judgment unit 40 will be described.

In the second abnormality judgment unit 20, the time ratio obtainment 22 obtains time ratio Rtx (Rtx=Ti/Tw or Rtx=Td/Tw). The time ratio Rtx is the ratio of time T1, in which the value of the time-course data is increasing, or time Td, in which the value of the time-course data is decreasing, with respect to total time Tw, in which the time-course data is obtained. The time ratio comparison judgment unit 24 judges that the time-course data is abnormal when the obtained time ratio Rtx deviates from range Rto of time ratios, which is stored in the time ratio storage unit 26. In other words, it is judged that the position of the sample material 201 is shifted with respect to the rotary disk 210 (sample table). Further, signal Sb indicating that a position shift is present is output.

Here, when the obtained time ratio Rtx does not deviate from the range Rto of time ratios, which is stored in the time ratio storage unit 26, it is not judged that the time-course data is abnormal. In other words, it is not judged that the position of the sample material 201 is shifted with respect to the rotary disk 210 (sample table). Therefore, signal Sb, which indicates that a position shift is present, is not output.

Further, time Ti, in which the value of the time-course data is increasing, and time Td, in which the value of the time-course data is decreasing, may be obtained by using differential values (difference values) of the time-course data Dt1, Dt2, Dt3, . . . .

The predetermined range Rto of time ratios, which is stored in the time ratio storage unit 26, is determined so that normal time-course data, which is obtained by normal measurement, and abnormal time-course data, which is obtained when the measurement is not carried out normally, can be distinguished from each other.

Specifically, a time-series change in the values of normal time-course data is stable, and the ratio of a time period in which the value of the time-course data is increasing or a time period in which the value of the time-course data is decreasing with respect to the total time period, in which the time-course data is obtained, seldom deviates from a predetermined range. Therefore, this predetermined range can be determined as the range Rto of the time ratios. The range Rto of the time ratios, which has been determined as described above, is input to the time ratio storage unit 26 and stored therein.

Further, in the third abnormality judgment unit 30, the increase/decrease obtainment unit 32 obtains the number of times of increase/decrease of the value of the time-course data and the order of increase/decrease thereof. The increase/decrease comparison judgment unit 34 receives the number of times of increase/decrease of the values of the time-course data Dt1, Dt2, Dt3, . . . , and the order of increase/decrease thereof. The time-course data Dt1, Dt2, Dt3, . . . is values D1, D2, D3, . . . representing the densities of the sample material 201. When at least one of the number Nx of times of increase/decrease and the order Px of increase/decrease differs from the number No of times of increase/decrease and the order Po of increase/decrease that are stored in the increase/decrease storage unit 36, the increase/decrease comparison judgment unit 34 judges that the time-course data Dt1, Dt2, Dt3, . . . is abnormal. In other words, the increase/decrease comparison judgment unit 34 judges that a position shift of the sample material with respect to the rotary disk 210 (sample table) is present. Further, the increase/decrease comparison judgment unit 34 outputs signal Sc, which indicates that a position shift has occurred.

Here, if both of the number Nx of times of increase/decrease and the order Px of increase/decrease are the same as the number No of times of increase/decrease and the order Po of increase/decrease, respectively, the increase/decrease comparison judgment unit 34 does not judge that the time-course data Dt1, Dt2, Dt3, . . . is abnormal. In other words, the increase/decrease comparison judgment unit 34 does not judge that a position shift of the sample material 201 with respect to the rotary disk 210 (sample table) is present. Therefore, the increase/decrease comparison judgment unit 34 does not output signal Sc, which indicates that a position shift has occurred.

The number Nx of times of increase/decrease and the order Px of increase/decrease may be obtained by using differential values (difference values) of the time-course data Dt1, Dt2, Dt3, . . . .

Further, the predetermined number No of times of increase/decrease and the predetermined order Po of increase/decrease, which are stored in the increase/decrease storage unit 36, are set so that normal time-course data, which is obtained when measurement is carried out normally, and abnormal time-course data, which is obtained when measurement is carried out abnormally, can be distinguished from each other.

Specifically, a time-series change in the values of normal time-course data is stable, and the number of times of increase/decrease of the normal time-course data and the order of increase/decrease thereof seldom differ from a predetermined number of times of increase/decrease and a predetermined order of increase/decrease, respectively. Therefore, the predetermined number of times of increase/decrease and the predetermined order of increase/decrease may be set as the predetermined number No of times of increase/decrease and the predetermined order Po. The predetermined number No of times of increase/decrease and the predetermined order Po, which have been obtained as described above, are input to the increase/decrease storage unit 36.

The predetermined number No of times of increase/decrease may be a combination of at least two numbers of times that are different from each other.

Further, in the fourth abnormality judgment unit 40, the power ratio obtainment unit 42 obtains power ratio Rpx (Rpx=Pf/Pw), which is the ratio of power Pf of a power spectrum in a frequency range that is higher than or equal to predetermined frequency $f_0$ with respect to the total power Pw of the power spectrum. The power spectrum has been obtained by performing Fourier transformation on the time-course data Dt1, Dt2, Dt3, . . . . When the obtained power ratio Rpx exceeds threshold value Rpo, which has been stored in advance in the power ratio storage unit 46, the power ratio comparison judgment unit 44 judges that the time-course data Dt1, Dt2, Dt3, . . . is abnormal. In other words, the power ratio comparison judgment unit 44 judges that a position shift of the sample material 201 with respect to the rotary disk 210 (sample table) is present. Further, the power ratio comparison judgment unit 44 outputs signal Sd, which indicates that a position shift has occurred.

Here, if the obtained power ratio Rpx does not exceed the threshold value Rpo, which has been stored in advance in the power ratio storage unit 46, the power ratio comparison judgment unit 44 does not judge that the time-course data Dt1, Dt2, Dt3, . . . is abnormal. In other words, the power ratio comparison judgment unit 44 does not judge that a position shift of the sample material 201 with respect to the rotary disk 210 (sample table) is present. Therefore, the power ratio comparison judgment unit 44 does not output signal Sd, which indicates that a position shift has occurred.

The predetermined threshold value Rpo, which is stored in the power ratio storage unit 46, is set so that normal time-course data, which is obtained when measurement is performed normally, and abnormal time-course data, which is obtained when measurement is carried out abnormally, can be distinguished from each other.

Specifically, the fluctuation of a time-series change in the values of normal time-course data is small and smooth. Therefore, when a power spectrum of normally-measured time-course data is obtained by performing Fourier transformation on the time-course data, the ratio of the power of a spectrum in a frequency range that is higher than or equal to predetermined frequency $f_0$ with respect to the total power of the power spectrum seldom exceeds the predetermined value. Therefore, the predetermined number may be set as the predetermined threshold value Rpo. The threshold value Rpo that has been set as described above is input to the power ratio storage unit 46 and stored therein.

In the first through fourth abnormality judgment units, when one of signals Sa, Sb, Sc and Sd, which indicate that a position shift of the sample material 201 with respect to the rotary disk 210 (sample table) has occurred, is output, this output signal is input to the alarm 90. The alarm 90 warns that the position of the sample material 201 is shifted with respect to the rotary disk 210 (sample table) by voice or by displaying information on the screen.

Alternatively, command (instruction) SS for remeasuring the time-course data may be output from the alarm 90 to the controller 500. Then, the controller 500 that has received the command SS may control the operation so that remeasurement is carried out for the measurement in which the abnormality in the time-course data occurred.

Next, the time-course data measurement apparatus 200 will be described. The time-course data measurement apparatus 200 includes a rotation shaft 260, which is driven by a rotary motor 250, a rotary disk 210, which is supported by the rotation shaft 260, four reaction cells 205, sample materials 201, and an optical meter (an optical measurement apparatus or a light measurement apparatus). The four reaction cells 205 are arranged on the rotary disk 210 along the circumference thereof at regular intervals. The sample materials 201 are placed in the respective reaction cells 205, and each of the sample materials 201 includes a reagent and blood. The optical meter 220 is fixed onto a position at which a change in the density of each of the sample materials is measured.

In each of the reaction cells 205, a different reagent, such as a reagent for assaying glucose and a reagent for assaying calcium, has been deposited (placed) in advance. After blood is dispensed (put or dripped) into each of the reaction cells 205 in which the reagents have been deposited, a change in the density of the sample material 201 including the reagent and the blood in each of the reaction cells is repeatedly measured by the optical meter 220. The measurement is carried out at regular intervals, for example, every eight seconds.

Specifically, the reaction cells 205 are moved to the measurement target range 220S of the optical meter 220, every two seconds, by rotation of the rotary disk 210. Then, a change in the density of the sample material 201 in each of the reaction cells 205 is measured by the optical meter 220.

Here, when attention is focused, for example, on a reaction cell 205a in which a reagent for assaying glucose has been deposited, measurement is performed in the following manner. The reaction cell 205a is moved to the measurement target range 220S of the optical meter 220 by rotation of the rotary disk 210, which is driven by the rotary motor 250, every eight seconds. Accordingly, a change in the densities of the sample material 201a in the reaction cell 205a is measured intermittently (every eight seconds) by the optical meter 220, and the time-course data Dt1, Dt2, Dt3, . . . is obtained. Each of the time-course data Dt1, Dt2, Dt3, . . . , which is obtained every eight seconds as described above, is obtained by measuring the density of the same sample material, for example, the sample material 201a in the reaction cell 205a, every eight seconds.

As described above, the time-course data measurement apparatus 200 can substantially simultaneously obtain time-course data for each of the four kinds of sample materials 401 that are placed in the four kinds of reaction cells 205, respectively.

Next, attention will be focused on one of the four kinds of sample materials on which measurement is performed substantially simultaneously, and the action of the position shift judgment apparatus 100 and the action of the time-course data measurement apparatus 200 will be described.

First, in the time-course measurement apparatus 200, blood 203a, which is a liquid, is dispensed on a reagent 202a in a dry state that is placed in a reaction cell 205a (in other words, the blood 203a is spot-deposited on the reagent 202a). The reaction cell 205a, in which the blood 203a is dispensed, is located on the opposite side of the measurement target range 220S of the optical meter 220 with respect to the rotation shaft 260 (a position at which the phase is shifted by 180 degrees). Then, a reaction of a sample material 201a including the reagent 202a and the blood 203a starts. After four seconds from the start of the reaction, the reaction cell 205a is moved to the measurement target range 220S of the optical meter 220 by rotation of the rotary disk 210. Then, the first density measurement is carried out on the sample material 201a by the optical meter 220. The first density measurement is carried out at time t1, and value D1, which represents the density of the sample material 201a, is obtained. In other words, time-course data Dt1 (t1, D1) is obtained.

Further, the optical meter 220 includes a light source 220L for measuring the density value of the sample material 201 and a light receiving unit 220J. The light source 220L outputs illumination light Ls and illuminates the sample material 201 that is placed in a transparent reaction cell on the rotary disk 210 from a position below the sample material 201. Here, an opening 210E is formed in an area of the rotary disk 210, the area corresponding to the sample material 201 placed at the center of each of the reaction cells 205. Therefore, the illumination light Ls is incident on the sample material 201 through the opening 210E.

The illumination light that has been output from the light source 220L and passed through the reaction cell 205 is reflected by the sample material 201. Then, reflection light Lh is output downward through the reaction cell 205 also through the reaction cell 205. Then, the light receiving unit 220J receives the reflection light Lh and performs opto-electrical conversion on the reflection light Lh to obtain an electrical signal. The optical meter 220 converts the electrical signal that has been obtained by the light receiving unit 220J into a value representing the density of the sample material 201. Accordingly, time-course data that indicates time at which the density of the sample material 201 was measured and the density value obtained by the measurement is output one by one.

Meanwhile, the type of the optical meter is not limited to the reflection type as described above. Illumination light that has been output from a light source that is arranged on the lower side of the transparent reaction cell 205 may be caused to enter the reaction cell 205. Then, transmission light, which has passed through the reaction cell 205 and the sample material 201 and output toward the upper side of the sample material 201, may be detected by the light receiving unit. In such a case, the light source and the light receiving unit are arranged on either side of the reaction cell in such a manner that they face each other.

After then, every time when the rotary disk 210 makes one complete rotation, in other words, every eight seconds, the optical meter 220 measures the density of the sample material 201a, and time-course-data Dt1, Dt2, Dt3, . . . is obtained.

Here, it is assumed that the rotary disk 210 accurately rotates. In other words, the rotary disk 210 accurately makes one complete rotation every eight seconds without causing any errors in the rotation. Then, judgment is made as to whether a fluctuation in the position (position shift) of the sample material 201a, which is placed on the rotary disk 210, with respect to the rotary disk 210 is present.

The time-course-data Dt1, Dt2, Dt3, . . . , which has been obtained as described above, is output, one by one, to the position shift judgment apparatus 100 and a data analysis unit 280.

The data analysis unit 280 may be provided in the position shift judgment apparatus 100. Alternatively, the data analysis unit 280 may be provided in the time-course data measurement apparatus 200. Further, the data analysis unit 280 may be provided separately from the position shift judgment apparatus 100 and the time-course data measurement apparatus 200.

The data analysis unit 280 analyzes the time-course data Dt1, Dt2, Dt3, . . . and assays grape sugar (dextrose or D-glucose) in blood 203a contained in the sample material 201a. The result of the assay of the grape sugar at the data analysis unit 280 is displayed at a display unit 285.

Meanwhile, the time-course data Dt1, Dt2, Dt3, . . . that has been input to the position shift judgment apparatus 100 is input, one after another, to each of the first abnormality judgment unit 10, the second abnormality judgment unit 20, the third abnormality judgment unit 30 and the fourth abnormality judgment unit 40 in the position shift judgment apparatus 100.

When the time-course data Dt1, Dt2, Dt3, . . . is input to the first abnormality judgment unit 10, the first abnormality judgment unit 10 compares the standard deviation value $\sigma x$ obtained for the time-course data Dt1, Dt2, Dt3, . . . with a predetermined threshold value $\sigma o$. When the first abnormality judgment unit 10 judges that the time-course data is abnormal, the first abnormality judgment unit 10 outputs signal Sa, which indicates that a position shift of the sample material 201 with respect to the rotary disk 210 (sample table) has occurred (hereinafter, simply referred to as "occurrence or presence of a position shift of a sample material").

When the time-course data Dt1, Dt2, Dt3, . . . is input to the second abnormality judgment unit 20, the second abnormality judgment unit 20 compares the time ratio Rtx obtained for the time-course data Dt1, Dt2, Dt3, . . . with a predetermined range Rto of time ratios. When the second abnormality judgment unit 20 judges that the time-course data is abnormal, the second abnormality judgment unit 20 outputs signal Sb, which indicates that a position shift of the sample material has occurred.

When the time-course data Dt1, Dt2, Dt3, . . . is input to the third abnormality judgment unit 30, the third abnormality judgment unit 30 compares the number Nx of times of increase/decrease and the order Px of increase/decrease that have been obtained for the time-course data Dt1, Dt2, Dt3, . . . with a predetermined number No of times of increase/decrease and the order Po of increase/decrease, respectively. When the third abnormality judgment unit 30 judges that the time-course data is abnormal, the third abnormality judgment unit 30 outputs signal Sc, which indicates that a position shift of the sample material has occurred.

When the time-course data Dt1, Dt2, Dt3, . . . is input to the fourth abnormality judgment unit 40, the fourth abnormality judgment unit 40 compares the power ratio Rpx obtained for the time-course data Dt1, Dt2, Dt3, . . . with a predetermined threshold value Rpo. When the fourth abnormality judgment unit 40 judges that the time-course data is abnormal, the fourth abnormality judgment unit 40 outputs signal Sd, which indicates that a position shift of the sample material has occurred.

When a signal indicating occurrence of a position shift of a sample material is output from at least one of the four kinds of abnormality judgment units, namely the first through fourth abnormality judgment units, the signal is input to the alarm 90. Then, the alarm 90 warns that a position shift of the sample material has occurred or requests the controller 500 to control the operation so that time-course data is remeasured.

Next, cases of judging the abnormality of the measured time-course data by using the four kinds of abnormality judgment units, namely the first through fourth abnormality judgment units will be specifically described.

In FIGS. 3 through 6, the vertical axis represents the density value Ob (Optical Density) of the sample material, and the horizontal axis represents time t (t-Ob coordinate). In each of FIGS. 3 through 6, normal time-course data and time-course data for comparison are expressed in the coordinate.

In FIGS. 3 through 6, normal time-course data, which has been measured correctly, is represented by signs At1, At2, At3, . . . , and time-course data for comparison is represented by signs Zt1, Zt2, Zt3, . . . . In FIGS. 3 through 6, normal time-course data that have various patterns are represented by the same signs At1, At2, At3, . . . , and the time-course data for comparison that have various patterns are represented by the same signs Zt1, Zt2, Zt3, . . . .

Figure 3:
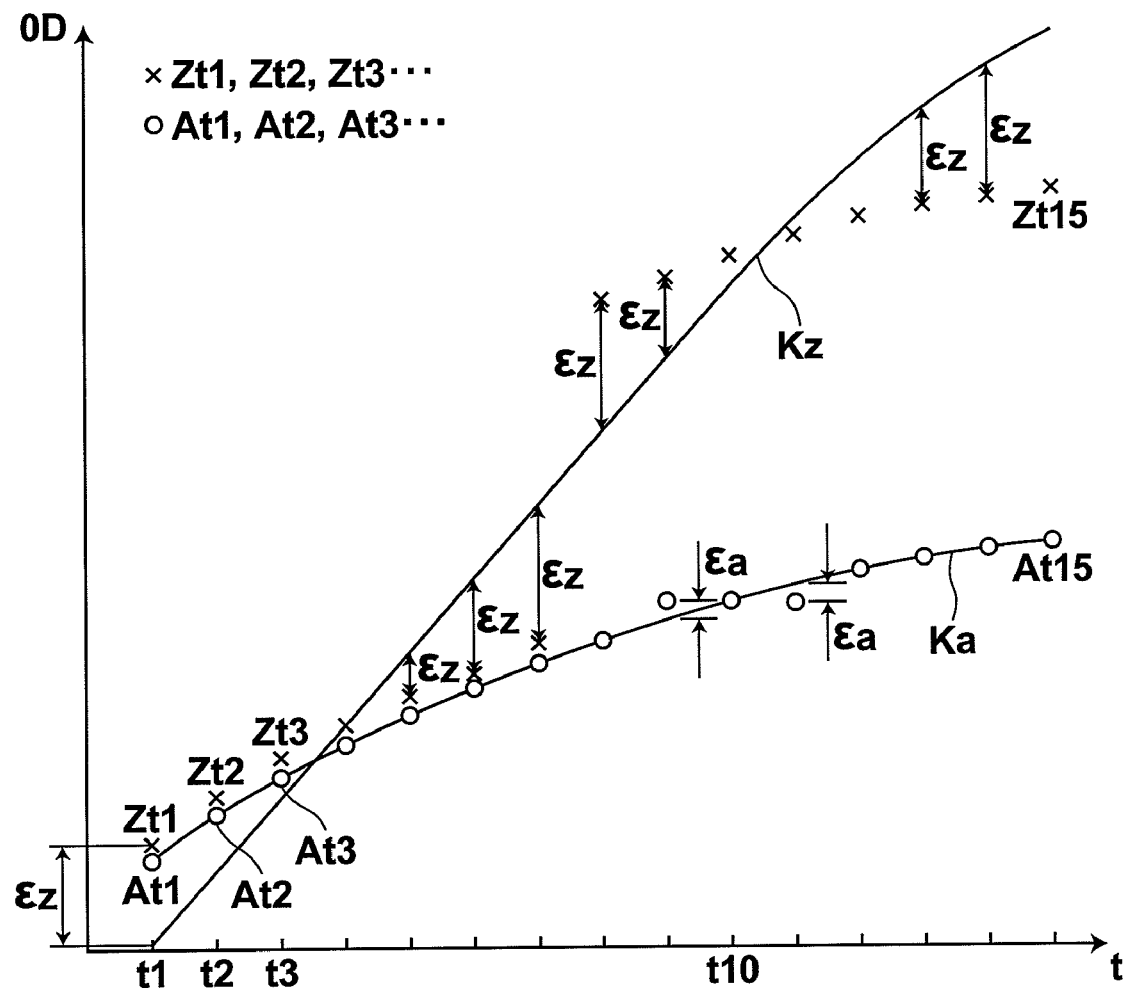
FIG. 3 is a diagram illustrating a regression curve that approximates normal time-course data and a regression curve that approximates time-course data for comparison.

In FIG. 3, normal time-course data At1, At2, At3, . . . in which the density value monotonously increases and time-course data Zt1, Zt2, Zt3, . . . for comparison are illustrated. The density value of the time-course data Zt1, Zt2, Zt3, . . . for comparison monotonously increases. However, the density value of the time-course data Zt1, Zt2, Zt3, . . . discontinuously shifts to the increase side at some part of the measurement. Here, the time-course data Zt1, Zt2, Zt3, . . . is not data that changes smoothly with a small fluctuation.

A case in which the time-course data as described above is input to the first abnormality judgment unit 10 will be described. The first abnormality judgment unit 10 judges the abnormality of the time-course data by using the value of a standard deviation of the approximation error of a regression curve with respect to the time-course data, the regression curve having been obtained by approximating the time-course data by a quadratic function.

The locus of the regression curve Ka, in which the normal time-course data At1, At2, At3, . . . has been approximated by a quadratic function, is substantially the same as the time-course data At1, At2, At3, . . . . Therefore, the value $\sigma x$ of the standard deviation that represents the deviation of the approximation error $\epsilon a$ of the regression curve Ka with respect to the time-course data At1, At2, At3, . . . is an extremely small value. Specifically, the predetermined threshold value $\sigma o$ is set at an extremely small value.

Meanwhile, the locus of the regression curve Kz, in which the time-course data Zt1, Zt2, Zt3, . . . for comparison is approximated by a quadratic function is greatly different from the time-course data Zt1, Zt2, Zt3, . . . . In other words, the quadratic function is insufficient to follow the data in which the density value is discontinuously shifted in the increase direction. Therefore, the magnitude and the deviation of the approximation error are large.

Therefore, the value $\sigma x$ of the standard deviation that represents the deviation of the approximation error $\epsilon z$ of the regression curve Kz with respect to the time-course data Zt1, Zt2, Zt3, . . . is a large value. Since the value $\sigma x$ of the standard deviation obtained for the time-course data Zt1, Zt2, Zt3, . . . exceeds the predetermined threshold value $\sigma o$, it is judged that the time-course data is abnormal.

Figure 4:
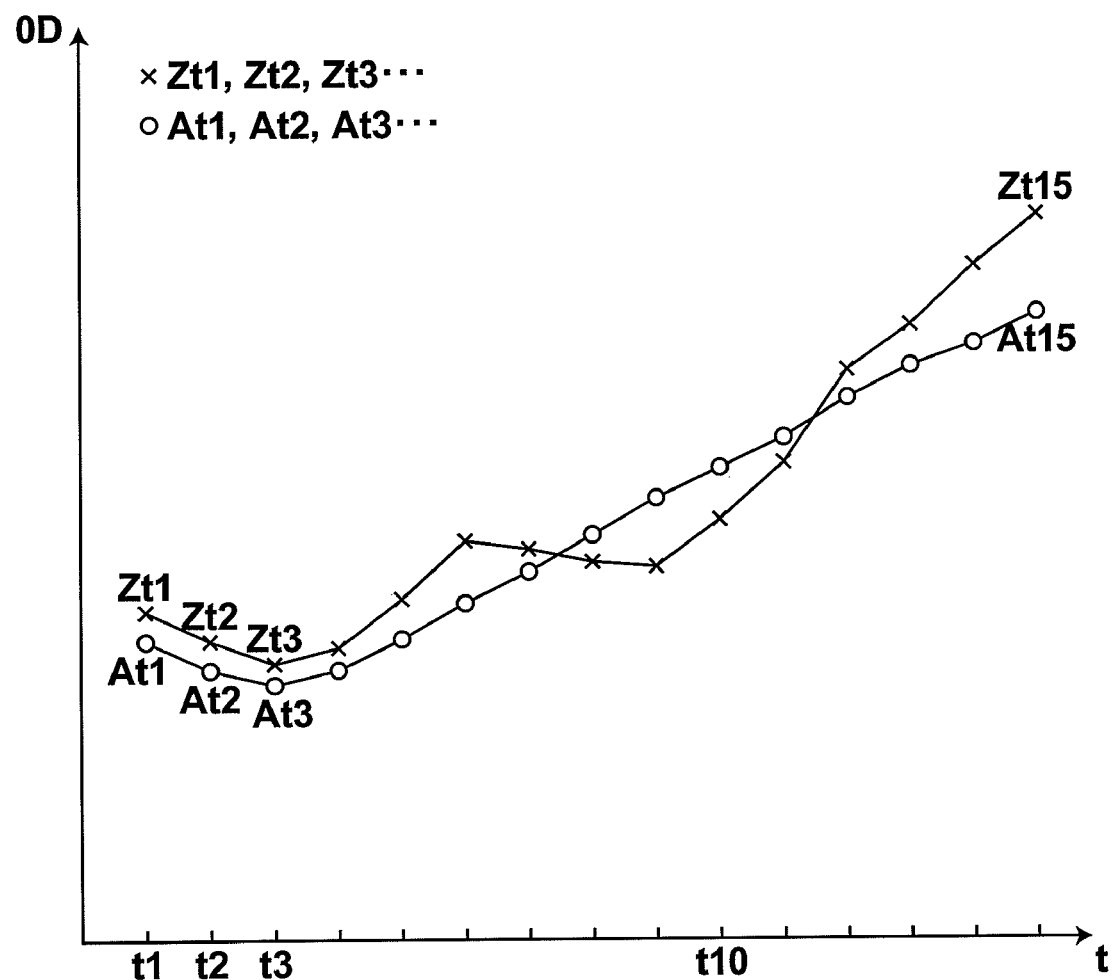
FIG. 4 is a diagram illustrating normal time-course data that is judged by a second abnormality judgment unit and time-course data for comparison.

In FIG. 4, normal time-course data At1, At2, At3, . . . and time-course data Zt1, Zt2, Zt3, . . . for comparison are expressed in the coordinate t-Ob. In FIG. 4, the density value of the normal time-course data At1, At2, At3, . . . temporarily decreases immediately after start of measurement and monotonously increases after the decrease. The density value of the time-course data Zt1, Zt2, Zt3, . . . for comparison temporarily decreases immediately after start of measurement. The density value of the time-course data Zt1, Zt2, Zt3, . . . for comparison increases as a whole, but decreases at some part of the measurement. Here, the time-course data Zt1, Zt2, Zt3, . . . is not data that changes smoothly with a small fluctuation.

A case in which the time-course data as described above is input to the second abnormality judgment unit 20 will be described. The second abnormality judgment unit 20 judges presence of a position shift of the sample material by judging the abnormality of the time-course data based on a ratio of a time period in which the value of the time-course data is increasing or decreasing with respect to the total time in which the time-course data is obtained.

Here, it is assumed that the time-course data is obtained 15 times at regular time intervals.

As illustrated in FIG. 4, the value of the normal time-course data At1, At2, At3, . . . decreases only in the first two measurement periods at the beginning of the 15 measurements. After then, the value of the time-course data continues to increase. Therefore, the ratio Rtx of a time period in which the value of the time-course data is decreasing with respect to the total time period of obtaining the time-course data is Rtx=2/14.

Meanwhile, the time-course data Zt1, Zt2, Zt3, . . . for comparison decreases in the first two measurement periods at the beginning of the 15 measurements. Further, the time-course data Zt1, Zt2, Zt3, . . . for comparison decreases three times in the later measurements. Therefore, the ratio Rtx of a time period in which the value of the time-course data is decreasing with respect to the total time period of obtaining the time-course data is Rtx=5/14.

Here, if the range Rto of the predetermined time ratio is set, for example, at $1/14 \leq Rto \leq 3/14$, the time ratio Rtx (Rtx=2/14) for the normal time-course data At1, At2, At3, . . . is within the predetermined range Rto. Therefore, the time-course data is not judged to be abnormal. In contrast, the time ratio Rtx (Rtx=5/14) for the time-course data for comparison is not within the predetermined range Rto. Therefore, the time-course data for comparison is judged to be abnormal.

Figure 5:
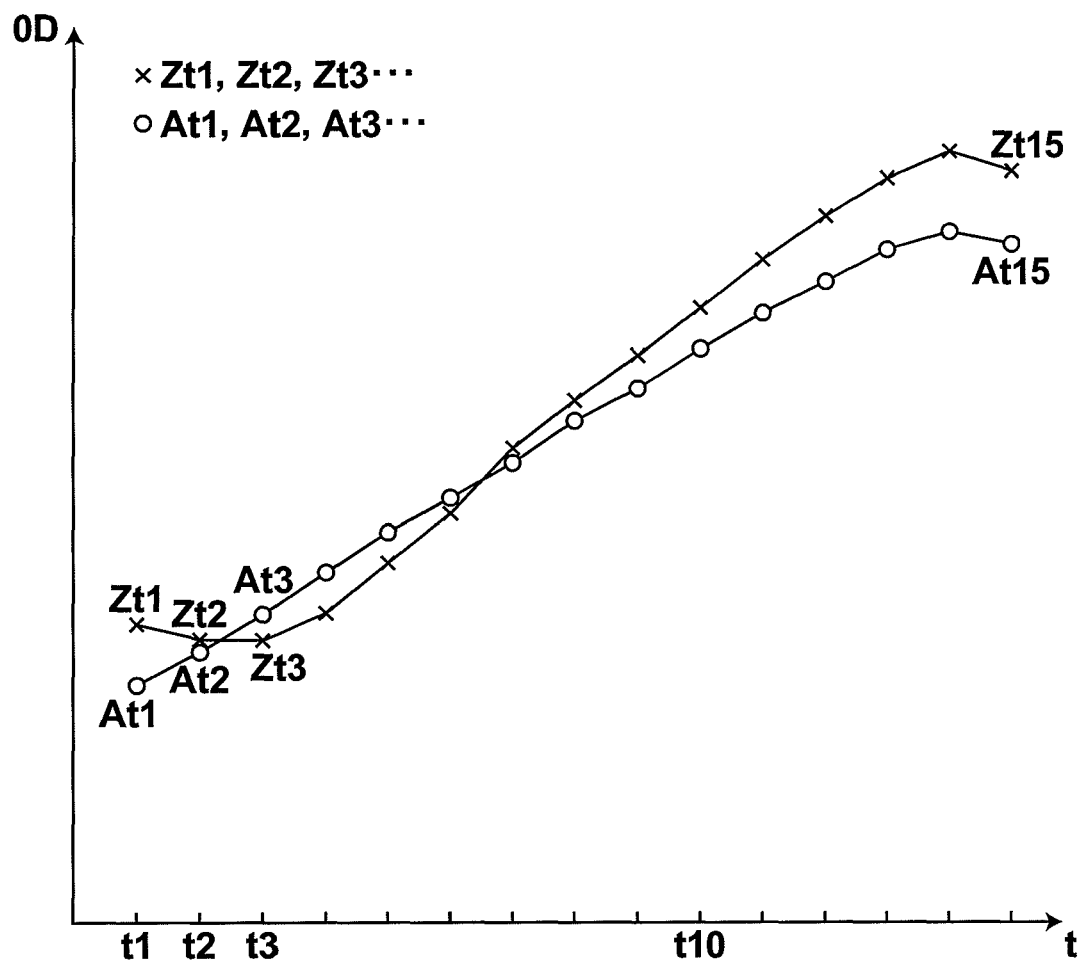
FIG. 5 is a diagram illustrating normal time-course data that is judged by a third abnormality judgment unit and time-course data for comparison.

FIG. 5 is a diagram illustrating normal time-course data At1, At2, At3, . . . and time-course data Zt1, Zt2, Zt3, . . . for comparison on the t-Ob coordinate. The density value of the normal time-course data At1, At2, At3, . . . monotonously increases immediately after start of measurement and decreases at the end of the measurement. The density value of the time-course data Zt1, Zt2, Zt3, . . . for comparison temporarily decreases immediately after start of measurement and monotonously increases. Further, the density value of the time-course data Zt1, Zt2, Zt3, . . . for comparison deceases at the end of the measurement. Here, the time-course data Zt1, Zt2, Zt3, . . . is not data that represents a smooth change that has a small fluctuation.

A case in which these sets of time-course data are input to the third abnormality judgment unit 30 will be described. The third abnormality judgment unit 30 judges presence of the position shift of the sample material by judging the abnormality of the time-course data based on the number of times of increase/decrease of the values of the time-course data and the order of increase/decrease.

As illustrated in FIG. 5, the number Nx of times of increase/decrease of the normal time-course data At1, At2, At3, . . . is two (Nx=2), because the value of the data increases first and decrease after the increase. Further, the order Px of increase/decrease is classified as Px=+1, because the fluctuation pattern of the data starts with an increase. If the fluctuation pattern of the time-course data starts with a decrease, the order Px is classified as Px=−1.

Meanwhile, the number Nx of times of increase/decrease of the time-course data Zt1, Zt2, Zt3, . . . is three (Nx=3), because the value of the data decreases first, increases after the decrease, and further decreases after the increase. Further, the order Px of increase/decrease is classified as Px=−1, because the fluctuation pattern of the data starts with a decrease.

Here, if the predetermined number No of times of increase/decrease is two (No=2) and the predetermined value Po of the order of increase/decrease is Po=+1 because the pattern starts with an increase, the number Nx of times of increase/decrease of the time-course data for comparison (Nx=3) differs from the predetermined number No of times of increase/decrease (No=2). Further, the order Px of increase/decrease for the time-course data for comparison (Px=−1) differs from the predetermined order Po of increase/decrease (Po=+1). At least one of the number of times of increase/decrease and the order of increase/decrease of the time-course data for comparison differs from the predetermined number of times of increase/decrease and the predetermined order of increase/decrease, respectively. Therefore, the time-course data for comparison is judged to be abnormal.

Meanwhile, both of the number Nx of times of increase/decrease of the normal time-course data At1, At2, At3, . . . and the order of increase/decrease of the normal time-course data are the same as the predetermined number No of times of increase/decrease and the predetermined order Po of increase/decrease, respectively. Therefore, the time-course data At1, At2, At3, . . . is not judged to be abnormal.

Figure 6:
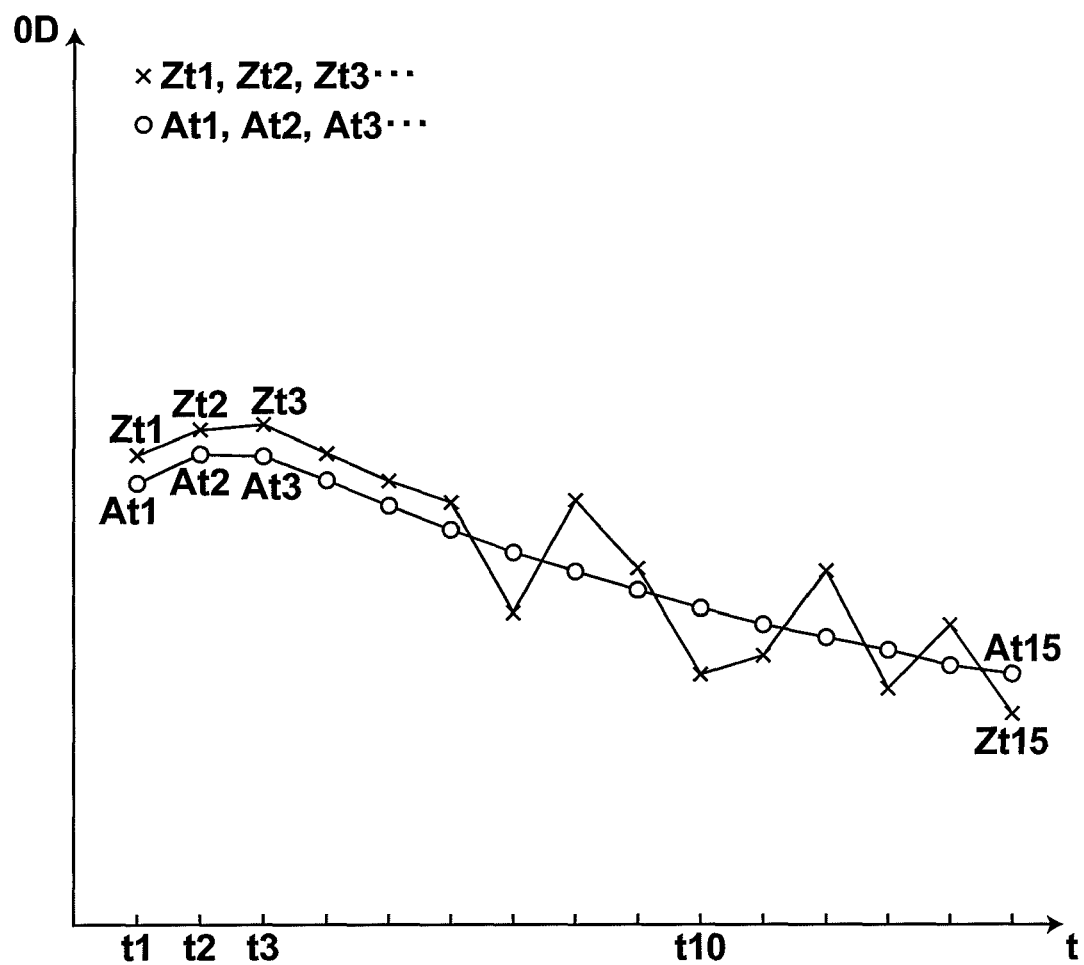
FIG. 6 is a diagram illustrating normal time-course data that is judged by a fourth abnormality judgment unit and time-course data for comparison.

FIG. 6 is a diagram illustrating normal time-course data At1, At2, At3, . . . and time-course data Zt1, Zt2, Zt3, . . . for comparison on the t-Ob coordinate. The density value of the normal time-course data At1, At2, At3, . . . temporarily increases immediately after start of measurement and monotonously decreases after the increase. The density value of the time-course data Zt1, Zt2, Zt3, . . . for comparison temporarily increases immediately after start of measurement and monotonously decreases after the increase. Further, after the monotonous decrease, an increase and a decrease are repeated. The density value of the time-course data Zt1, Zt2, Zt3, . . . for comparison, as a whole, fluctuates along the normal time-course data. Here, the time-course data Zt1, Zt2, Zt3, . . . is not data that represents a smooth change that has a small fluctuation.

Figure 7A:
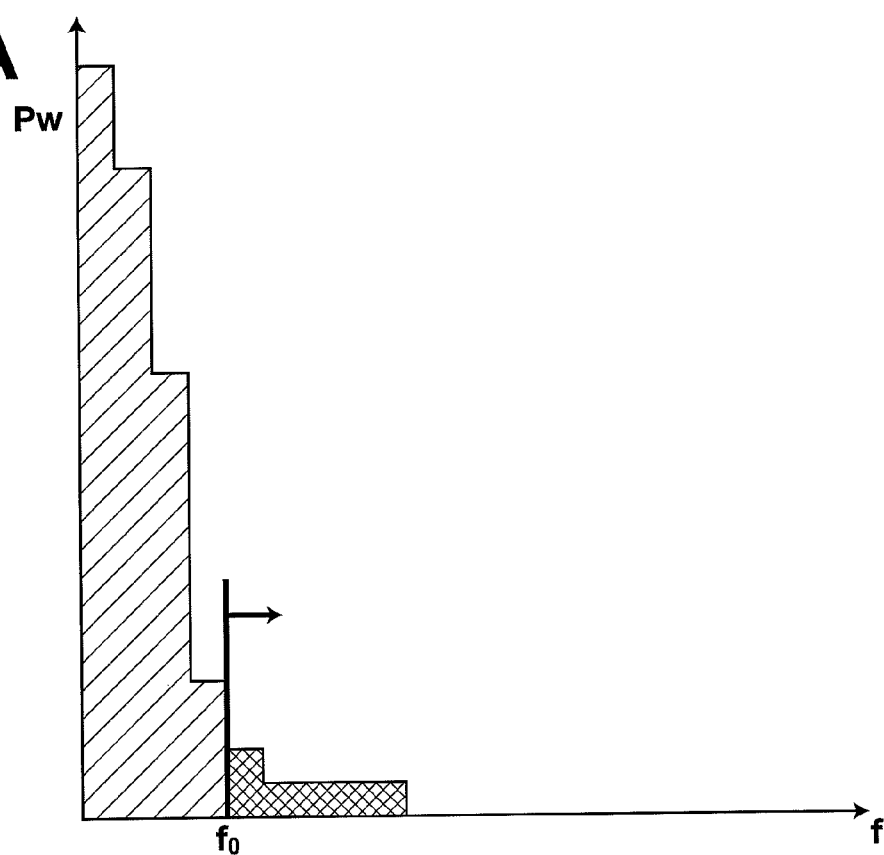
FIG. 7A is a diagram illustrating a power spectrum obtained by performing Fourier transformation on normal time-course data.
Figure 7B:
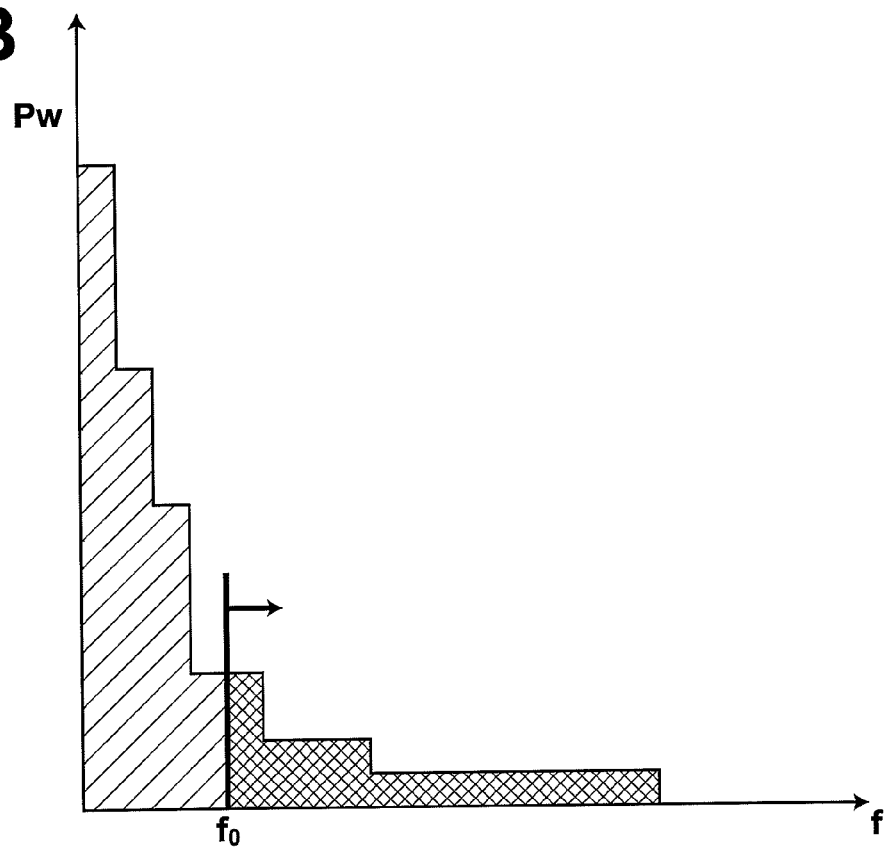
FIG. 7B is a diagram illustrating a power spectrum obtained by performing Fourier transformation on time-course data for comparison.

FIGS. 7A and 7B are diagrams illustrating power spectra obtained by performing Fourier transformation on normal time-course data and time-course data for comparison, respectively. In FIGS. 7A and 7B, the vertical axis of the coordinate represents the power and the horizontal axis of the coordinate represents the frequency. FIG. 7A is a diagram illustrating the power spectrum of the normal time-course data, and FIG. 7B is a diagram illustrating the power spectrum of the time-course data for comparison.

A case in which these sets of time-course data have been input to the fourth abnormality judgment unit 40 will be described. The fourth abnormality judgment unit 40 judges presence of the position shift of the sample material by judging the abnormality of the time-course data based on the power spectrum obtained by performing Fourier transformation on the time-course data.

The power ratio Rpx, which is the ratio of the power of a power spectrum in a frequency range that is higher than or equal to predetermined frequency $f_0$ with respect to the total power of the power spectrum, the power spectrum being obtained by performing Fourier transformation on the normal time-course data At1, At2, At3, . . . , is 0.05 (please refer to FIG. 7A).

Meanwhile, the power ratio Rpx, which is the ratio of the power of a power spectrum in a frequency range that is higher than or equal to the predetermined frequency $f_0$ with respect to the total power of the power spectrum, the power spectrum being obtained by performing Fourier transformation on the time-course data for comparison Zt1, Zt2, Zt3, . . . , is 0.25 (please refer to FIG. 7B).

Here, if the predetermined threshold value Rpo has been set at 0.1, the power ratio Rpx (Rpx=0.25) for the time-course data for comparison is greater than the predetermined threshold value Rpo (Rpo=0.1). Therefore, the time-course data for comparison is judged to be abnormal.

Meanwhile, the value of the power ratio Rpx (Rpx=0.5) with respect to the normal time-course data At1, At2, At3, . . . is less than or equal to the value of the predetermined threshold value Rpo (Rpo=0.1). Therefore, the time-course data is not judged to be abnormal.

Further, it is not necessary that the position shift judgment apparatus includes all of the four kinds of abnormality judgment units, namely, the first through fourth abnormality judgment units. The position shift judgment apparatus may include only one of the first through forth abnormality judgment units alone. Alternatively, the position shift judgment apparatus may include at least two of the first through forth abnormality judgment units in combination.

Here, the position shift judgment apparatus may include the first abnormality judgment unit 10 and at least one of the second abnormality judgment unit 20, the third abnormality judgment unit 30 and the fourth abnormality judgment unit 40 in combination.

Alternatively, the position shift judgment apparatus may include the second abnormality judgment unit 20 and at least one of the first abnormality judgment unit 10, the third abnormality judgment unit 30 and the fourth abnormality judgment unit 40 in combination.

Further, in the method and apparatus for judging a position shift according to the present invention, input time-course data may be sequentially judged by the four abnormality judgment units, namely the first through fourth abnormality judgment units. Then, when a judgment result that a position shift of a sample material is present is detected, the judgment as to whether a position shift of the sample material is present may end. Here, the sequential judgment operation by the four kinds of abnormality judgment units, the first through fourth abnormality judgment units, is controlled by the controller 500. At the same time, the judgment as to whether a position shift of the sample material is present is input to the controller 500 directly or through the alarm 90. The controller 500 controls the position shift judgment apparatus to end the process of judging the presence of the position shift of the sample material. Accordingly, it is possible to reduce the load on the first through fourth abnormality judgment units.

The aforementioned judgment may be made in any order. For example, the order may be the third abnormality judgment unit 30, the first abnormality judgment unit 10, the second abnormality judgment unit 20 and the fourth abnormality judgment unit 40. Alternatively, the order may be the first abnormality judgment unit 10, the second abnormality judgment unit 20, the third abnormality judgment unit 30 and the fourth abnormality judgment unit or the like.

In the position shift judgment method and apparatus of the present invention, the received time-course data may be simultaneously judged by the four kinds of abnormality judgment units, i.e., the first through fourth abnormality judgment units. Then, when one of the abnormality judgment units has output a judgment that the position of the sample material is shifted, the judgment as to the presence of the position shift of the sample material may end. Here, the judgment as to whether a position shift of the sample material is present may be input to the controller 500 directly or through the alarm 90. Then, the controller 500 can control the position shift judgment apparatus to end the process of judging the presence of the position shift of the sample material. Accordingly, it is possible to reduce the load on the first through fourth abnormality judgment units.

The aforementioned method for judging the abnormality of the time-course data may be applied not only to a case of intermittently (for example, every eight seconds) measuring the density of the sample material but to a case of continuously measuring the density of the sample material.

The present invention cannot judge, as abnormality of time-course data, all sets of time-course data that have not been measured normally. Therefore, abnormal time-course data, which has not been measured normally, may be included in the time-course data that has not been judged as the abnormal time-course data. In other words, there are cases in which even if time-course data is abnormal, the time-course data may not be judged to be abnormal in some cases. However, the present invention can still reduce overlooking of abnormality of the time-course data without erroneously judging normal time-course data as abnormal time-course data. Accordingly, it is possible to increase the reliability on the judgment as to the presence of the position shift of the sample material with respect to the sample table.

In the aforementioned embodiment, a case in which the position shift judgment apparatus judges, based on time-course data obtained by measuring the sample material 201 placed on the reaction cell 205, the presence of a position shift of the sample material 201 with respect to the rotary disk 210 (sample table) has been described. In other words, a case in which the position shift judgment apparatus judges presence of a position shift of the reaction cell 205, with which the sample material 201 is in close contact, with respect to the rotary disk 210 has been described. Here, a case in which a test target (assay target), which is a target of actual quantitative measurement (assay) of a component, is the same as the sample material for judging the presence of a position shift of the reaction cell 205 with respect to the rotary disk 210 has been described. However, it is not necessary that the test target and the sample material are the same. For example, the test target, which is the target of actual quantitative measurement of a component, and the sample material for judging the presence of a position shift of the reaction cell 205 with respect to the rotary disk 210 may be separately placed at different positions on the reaction cells 205. Then, the quantitative measurement of the component of the test target and the judgment as to the presence of the position shift by using the sample material may be carried out.

Figure 8:
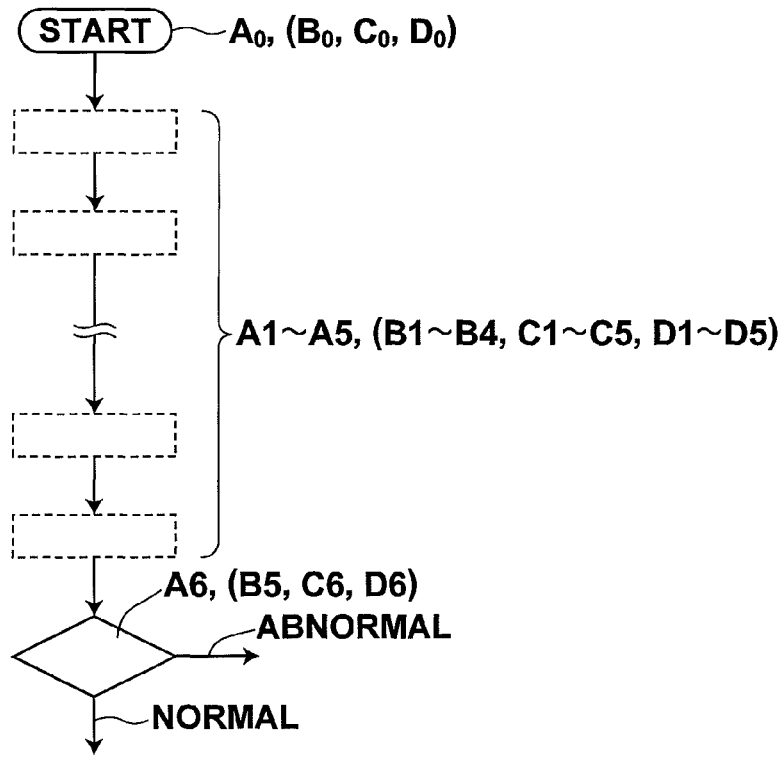
FIG. 8 is a flow chart of judgment methods 1 through 4.
Figure 9:
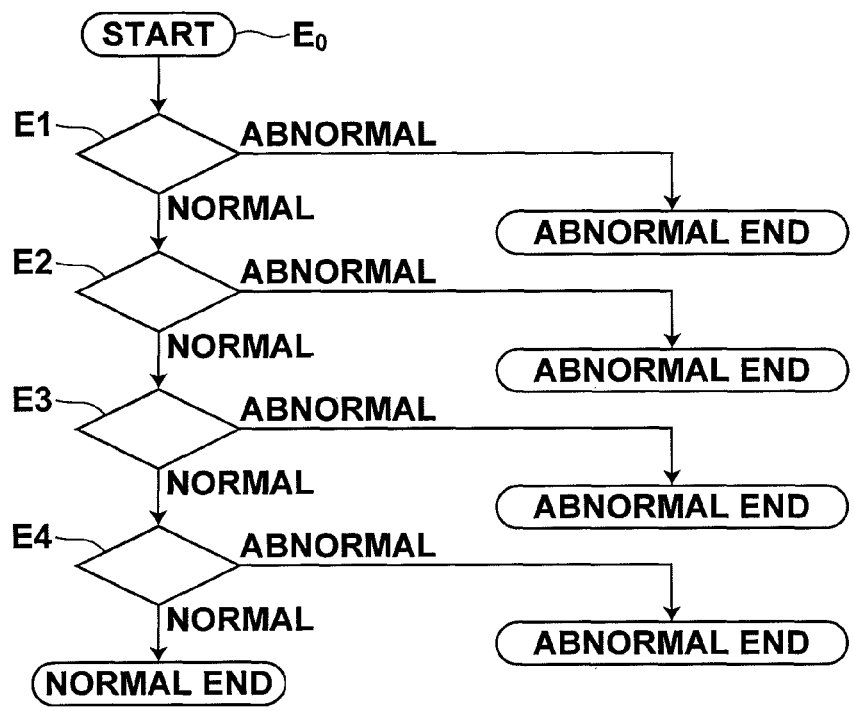
FIG. 9 is a flow chart of judgment method 5.

Next, a case of judging the abnormality of time-course data will be described with reference to the flow charts illustrated in FIGS. 8 and 9. FIG. 8 is a flow chart showing judgment methods 1 through 4 for judging whether time-course data is normal or abnormal. FIG. 9 is a flow chart showing judgment method 5. In the judgment method 5, the judgment methods 1 through 4 are combined with each other and normal-end or abnormal-end is judged for the time-course data.

The time-course data (discrete data) in time series is described as follows:

Time-Course Data: $D(t)$, $t=0$ to $N$. Note that "t" is a data number.

<Judgment Method 1>

In judgment method 1, time-course patterns are classified into an increase pattern, a decrease pattern, a convex pattern and a concave pattern. If the pattern is not a correct (normal) time-course pattern, it is judged that the time-course abnormality is present (please refer to FIG. 8). Signs $A_0$ through $A6$, which will be described later, correspond to the signs in the flow chart illustrated in FIG. 8.

[$A_0$]: Start.

[A1]: Specify a measurement item.

[A2]: Extract a normal time-course pattern of the relevant measurement item from a storage area (patterns are classified into an increase pattern, a decrease pattern, a convex pattern and a concave pattern).

[A3]: Divide the time-course data, in time series, into a beginning period, a middle period and an end period.

[A4]: Representative data (an average value or the like) for each of the beginning period, the middle period and the end period is obtained (Beginning-Period Average Value=$D0$, Middle-Period Average Value=$D1$, and End-Period Average Value=$D2$).

[A5]: If $D0<D1<D2$, it is estimated that the pattern is an "increase" pattern.

If $D0>D1>D2$, it is estimated that the pattern is a "decrease" pattern.

If $D0<D1>D2$, it is estimated that the pattern is a "convex" pattern.

If $D0>D1<D2$, it is estimated that the pattern is a "concave" pattern.

[A6]: If the estimation result coincides with the normal time-course pattern, it is judged that the time-course data is normal. If the estimation result does not coincide with the normal time-course pattern, it is judged that the time-course data is abnormal.

<Judgment Method 2>

In judgment method 2, the number of periods of increase and the number of periods of decrease are counted in time-course differential. In the time-course of an increase pattern, if the number of periods of decrease is greater than or equal to a threshold value, it is judged that the time-course data is abnormal. In the time-course of a decrease pattern, if the number of periods of increase is greater than or equal to a threshold value, it is judged that the time-course data is abnormal (please refer to FIG. 8). Note that signs $B_0$ through $B5$, which will be described later, correspond to the signs in the flow chart illustrated in FIG. 8.

[$B_0$]: Start.

[B1]: Specify a measurement item.

[B2]: Extract a normal time-course pattern of the relevant measurement item and a threshold value (Pt) from a storage area (patterns are classified into an increase pattern and a decrease pattern.)

[B3]: Perform differential (difference) operation (calculation).

$$\Delta D(t)=D(t)-D(t-1), t=1 \text{ to } N.$$

[B4]: If the normal time-course pattern of the relevant measurement item is an "increase" pattern, the number of sets of data satisfying $\Delta D(t)>0$ is counted and used as the number of periods of increase (Pi).

If the normal time-course pattern of the relevant measurement item is a "decrease" pattern, the number of sets of data satisfying $\Delta D(t)<0$ is counted and used as the number of periods of decrease (Pd).

[B5] If the normal time-course pattern of the relevant measurement item is an "increase" pattern, and $Pi \geq Pt$, the time-course data is judged to be normal. If the normal time-course pattern of the relevant measurement item is an "increase" pattern, and $Pi<Pt$, the time-course data is judged to be abnormal.

If the normal time-course pattern of the relevant measurement item is a "decrease" pattern, and $Pd>Pt$, the time-course data is judged to be normal. If the normal time-course pattern of the relevant measurement item is a "decrease" pattern, and $Pd<Pt$, the time-course data is judged to be abnormal.

<Judgment Method 3>

In judgment method 3, if the standard deviation of a time-course quadratic regression error exceeds a threshold value, it is judged that the time-course abnormality is present. Alternatively, if the standard deviation of an error from regression curve, such as n-th order power series regression, logarithm function regression and an index function regression, exceeds a threshold value, it is judged that the time-course abnormality is present (please refer to FIG. 8). Note that signs $C_0$ through $C6$, which will be described later, correspond to the signs in the flow chart illustrated in FIG. 8.

[$C_0$]: Start.

[C1]: Specify a measurement item.

[C2]: Extract a threshold value (Pt) of the relevant measurement item from a storage area.

[C3] A regression curve of the time-course data ($D(t)$) is obtained, and the value ($F(t)$) on the regression curve corresponding to each measurement point (t) is obtained.

[C4]: A regression error $\delta D(t)$ is obtained. Here, $\delta D(t)=D(t)-F(t)$.

[C5]: The standard deviation $\sigma$ of $\delta D(t)$ is obtained.

[C6]: If $\sigma \leq Pt$, it is judged that the time-course data is normal. If $\sigma>Pt$, it is judged that the time-course data is abnormal.

<Judgment Method 4>

In judgment method 4, Fourier transformation is performed on time-course data to obtain the power spectrum of the time-course data. Then, if the component that is higher than or equal to a specific frequency is greater than or equal to a threshold value, it is judged that time-course abnormality is present (please refer to FIG. 8). Note that signs $D_0$ through $D6$, which will be described later, correspond to the signs in the flow chart illustrated in FIG. 8.

[$D_0$]: Start.

[D1]: Specify a measurement item.

[D2]: Extract a threshold value (Pt) of the relevant measurement item from a storage area.

[D3]: Fourier transformation is performed on time-course data ($D(t)$) to obtain the power spectrum of the time-course data.

[D4]: The total integral value (sum) Sa of the power spectrum is obtained.

[D5]: The integral value (sum) Sf of the power spectrum in a frequency range that is higher than or equal to a predetermined frequency f is obtained.

[D6]: If Sf/Sa<Pt, it is judged that the time-course data is normal. If Sf/Sa>Pt, it is judged that the time-course data is abnormal.

<Judgment Method 5>

In judgment method 5, the judgment methods 1 through 4 are performed, one after another, from rough judgment, which requires a shorter time period for judgment, to accurate judgment, which requires a longer time period for judgment. Since the judgments are performed in such a manner, it is possible to reduce time required for judgment and to improve the accuracy of judgment (please refer to FIG. 9). Alternatively, in the judgment method 5, at least two of appropriate methods may be selected from the judgment methods 1 through 4 and used in combination. Alternatively, one of the judgment methods 1 through 4 may be used alone. Note that signs $E_0$ through E6, which will be described later, correspond to the signs in the flow chart illustrated in FIG. 9.

[$E_0$]: Start.

[E1]: Judgment is made by using the judgment method 1. If it is judged that the time-course data is abnormal, the process goes to abnormal-end processing (abnormal end). If it is judged that the time-course data is normal, the processing goes to judgment by using the judgment method 2 [E2].

[E2]: Judgment is made by using the judgment method 2. If it is judged that the time-course data is abnormal, the process goes to abnormal-end processing (abnormal end). If it is judged that the time-course data is normal, the processing goes to judgment by using the judgment method 3 [E3].

[E3]: Judgment is made by using the judgment method 3. If it is judged that the time-course data is abnormal, the process goes to abnormal-end processing (abnormal end). If it is judged that the time-course data is normal, the processing goes to judgment by using the judgment method 4 [E4].

[E4]: Judgment is made by using the judgment method 4. If it is judged that the time-course data is abnormal, the processing goes to abnormal-end processing (abnormal end). If it is judged that the time-course data is normal, the process goes to normal-end processing (normal end).

Figure 10:
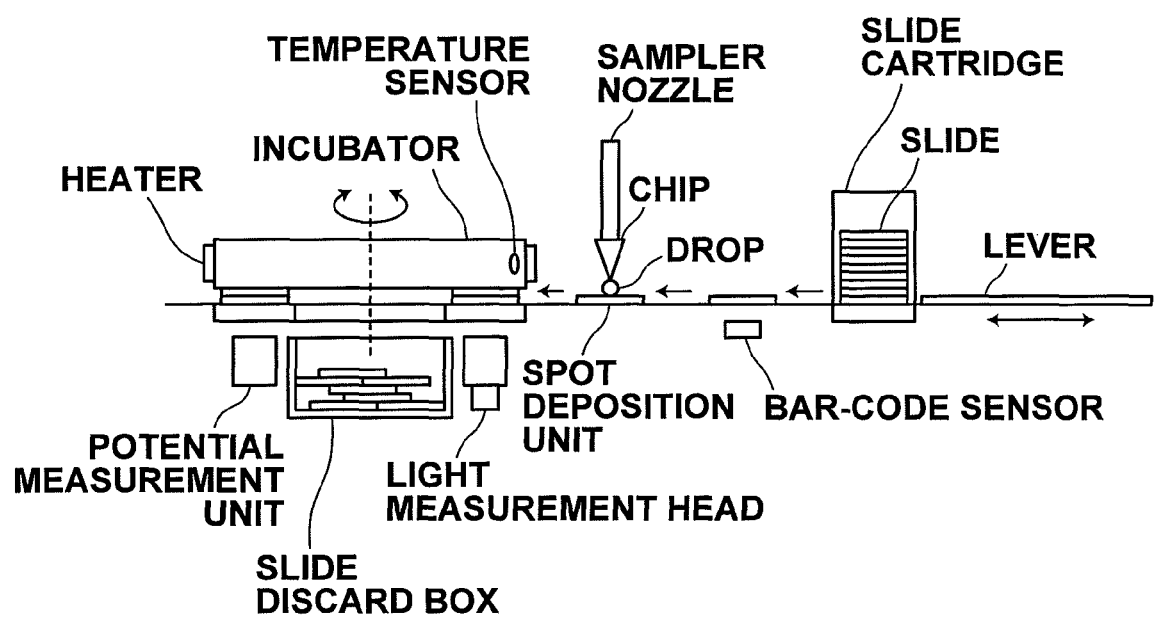
FIG. 10 is a diagram illustrating a manner in which time-course data is measured.

FIG. 10 is a diagram illustrating a manner in which time-course data is measured. In FIG. 10, measurement items are γGTP, amylase, lipase or the like, and time-course data with respect to blood, blood plasma, urine or the like that has been spot-deposited on a slide is measured.

Next, measurement of the time-course data will be outlined.

(1) Different kinds of slides are used for the respective measurement items (γGTP, amylase, lipase, and the like). Information about the use of the slide is included in bar-code information.

(2) A drop (measurement target: blood, blood plasma, urine or the like) is spot-deposited from a chip, and an area of the measurement target for a diameter of approximately 10 mm develops color.

(3) The slide is inserted into a disk within an incubator and measured by a light measurement head (optical measurement head) that has a diameter of approximately 6 mm.

(4) The slide is inserted into the disk within the incubator and kept at 37° C.

(5) A plurality of slides are held in the disk. The reflection density of each of the slides is measured every 7 to 9 seconds while the disk is rotated.

(6) When the disk is rotated, the positions at which the slides are held and the stop position of the disk may be shifted. If the positions are shifted, the diameter of measurement light, which is 6 mm in diameter, is not appropriately positioned within the color-developed portion, which is 10 mm in diameter. Therefore, accurate light measurement is not carried out (position shift).

(7) Since the plurality of slides are placed on the disk, some of them can be continued to be measured normally. In such a case, measurement is repeated till the end of operation, and a curve of a temporal density change (time course) is generated. Then, the smoothness of the curve is checked. If the curve is not smooth, it is judged that the time-course data is abnormal.

(8) A deviation in the measurement results is caused by a change in the light (luminance) of a light-source lamp because of the lifetime thereof, an electrical trouble or the like.

What is claimed is:

1. A method for judging a position shift of sample materials with respect to a sample table on which the sample materials are conveyed, comprising the following steps:

measuring by a measuring apparatus in time series a change in density of each of a plurality of sample materials by color reaction thereof by repeatedly conveying each of the plurality of sample materials to a measurement position by moving a sample table, on which the plurality of sample materials are placed;

measuring by a position shift judgment apparatus a value of a standard deviation representing the distribution of the approximation error of a regression curve that approximates the values of time-course data obtained by the measuring step; and determining by the position shift judgment apparatus whether the value is greater than a predetermined threshold value, in which case it is judged that a position shift of each of the sample materials with respect to the sample table is present.

2. A method for judging a position shift of sample materials with respect to a sample table on which the sample materials are conveyed, comprising the following steps:

measuring by a measuring apparatus a value in time series of a change in density of each of a plurality of sample materials by color reaction thereof by repeatedly conveying each of the plurality of sample materials to a measurement position by moving the sample table, on which the plurality of sample materials are placed;

measuring by a position shift judgment apparatus a ratio of a time period in which the value of the time-course data is increasing or a time period in which the value of the time-course data is decreasing with respect to the total time period in which the time-course data is being obtained; and determining by the position shift judgment apparatus whether the ratio deviates from a predetermined range of values, in which case it is judged that a position shift of the sample material with respect to the sample table is present.

3. An apparatus for judging a position shift, wherein when each of a plurality of sample materials is measured in time series by repeatedly conveying each of the plurality of sample materials to a measurement position by moving a sample table, on which the plurality of sample materials are placed, presence of a position shift of each of the plurality of sample materials with respect to the sample table is judged, the apparatus comprising:

a regression curve generation means for generating a regression curve that approximates time-course data obtained by measuring, in time series, a change in the density of each of the plurality of sample materials by a color reaction thereof;

a standard deviation obtainment means for obtaining the value of a standard deviation representing the distribution of the approximation error of the regression curve; and a standard deviation comparison judgment means for comparing the value of the standard deviation and a predetermined threshold value with each other, wherein when the value of the standard deviation is greater than the threshold value, the standard deviation comparison judgment means judges that a position shift of the sample material with respect to the sample table is present and outputs the result of the judgment.

4. An apparatus for judging a position shift, wherein when each of a plurality of sample materials is measured in time series by repeatedly conveying each of the plurality of sample materials to a measurement position by moving a sample table, on which the plurality of sample materials are placed, presence of a position shift of each of the plurality of sample materials with respect to the sample table is judged, the apparatus comprising:

a time ratio obtainment means for obtaining the ratio of a time period in which the value of time-course data is increasing or a time period in which the value of the time-course data is decreasing with respect to the total time period in which the time-course data is being obtained, the time-course data being obtained by measuring, in time series, a change in the density of each of the plurality of sample materials by a color reaction thereof; and a time ratio comparison judgment means for comparing the ratio and a predetermined range of values with each other, wherein when the ratio deviates from the predetermined range of values, the time ratio comparison judgment means judges that a position shift of the sample material with respect to the sample table is present and outputs the result of the judgment.

5. An apparatus for judging a position shift, as defined in claim 4, the apparatus further comprising:

a regression curve generation means for generating a regression curve that approximates the time-course data;

a standard deviation obtainment means for obtaining the value of a standard deviation representing the distribution of the approximation error of the regression curve with respect to the time-course data; and a standard deviation comparison judgment means for comparing the value of the standard deviation and a predetermined threshold value with each other, wherein when the value of the standard deviation is greater than the threshold value, the standard deviation comparison judgment means judges that a position shift of the sample material with respect to the sample table is present and outputs the result of the judgment.

6. An apparatus for judging a position shift, as defined in claim 3, the apparatus further comprising:

an increase/decrease obtainment means for obtaining the number of times of increase/decrease of the values of the time-course data and the order of increase/decrease thereof; and an increase/decrease comparison judgment means for comparing the obtained number of times of increase/decrease and the obtained order of increase/decrease with a predetermined number of times of increase/decrease and a predetermined order of increase/decrease, respectively, wherein when at least one of the obtained number of times of increase/decrease and the obtained order of increase/decrease differs from the predetermined number of times of increase/decrease and the predetermined order of increase/decrease, respectively, the increase/decrease comparison judgment means judges that a position shift of the sample material with respect to the sample table is present and outputs the result of the judgment.

7. An apparatus for judging a position shift, as defined in claim 4, the apparatus further comprising:

an increase/decrease obtainment means for obtaining the number of times of increase/decrease of the values of the time-course data and the order of increase/decrease thereof; and an increase/decrease comparison judgment means for comparing the obtained number of times of increase/decrease and the obtained order of increase/decrease with a predetermined number of times of increase/decrease and a predetermined order of increase/decrease, respectively, wherein when at least one of the obtained number of times of increase/decrease and the obtained order of increase/decrease differs from the predetermined number of times of increase/decrease and the predetermined order of increase/decrease, respectively, the increase/decrease comparison judgment means judges that a position shift of the sample material with respect to the sample table is present and outputs the result of the judgment.

8. An apparatus for judging a position shift, as defined in claim 5, the apparatus further comprising:

an increase/decrease obtainment means for obtaining the number of times of increase/decrease of the values of the time-course data and the order of increase/decrease thereof; and an increase/decrease comparison judgment means for comparing the obtained number of times of increase/decrease and the obtained order of increase/decrease with a predetermined number of times of increase/decrease and a predetermined order of increase/decrease, respectively, wherein when at least one of the obtained number of times of increase/decrease and the obtained order of increase/decrease differs from the predetermined number of times of increase/decrease and the predetermined order of increase/decrease, respectively, the increase/decrease comparison judgment means judges that a position shift of the sample material with respect to the sample table is present and outputs the result of the judgment.

9. An apparatus for judging a position shift, as defined in claim 3, the apparatus further comprising:

a power ratio obtainment means for obtaining the ratio of the power of a power spectrum in a frequency range that is higher than or equal to a predetermined frequency with respect to the total power of the power spectrum, the power spectrum being obtained by performing Fourier transformation on the time-course data; and a power ratio comparison judgment means for comparing the ratio and a predetermined threshold value with each other, wherein when the ratio is higher than the predetermined threshold value, the power ratio comparison judgment means judges that a position shift of the sample material with respect to the sample table is present and outputs the result of the judgment.

10. An apparatus for judging a position shift, as defined in claim 4, the apparatus further comprising:

a power ratio obtainment means for obtaining the ratio of the power of a power spectrum in a frequency range that is higher than or equal to a predetermined frequency with respect to the total power of the power spectrum, the power spectrum being obtained by performing Fourier transformation on the time-course data; and a power ratio comparison judgment means for comparing the ratio and a predetermined threshold value with each other, wherein when the ratio is higher than the predetermined threshold value, the power ratio comparison judgment means judges that a position shift of the sample material with respect to the sample table is present and outputs the result of the judgment.

11. An apparatus for judging a position shift, as defined in claim 5, the apparatus further comprising:

a power ratio obtainment means for obtaining the ratio of the power of a power spectrum in a frequency range that is higher than or equal to a predetermined frequency with respect to the total power of the power spectrum, the power spectrum being obtained by performing Fourier transformation on the time-course data; and a power ratio comparison judgment means for comparing the ratio and a predetermined threshold value with each other, wherein when the ratio is higher than the predetermined threshold value, the power ratio comparison judgment means judges that a position shift of the sample material with respect to the sample table is present and outputs the result of the judgment.

12. An apparatus for judging a position shift, as defined in claim 6, the apparatus further comprising:

a power ratio obtainment means for obtaining the ratio of the power of a power spectrum in a frequency range that is higher than or equal to a predetermined frequency with respect to the total power of the power spectrum, the power spectrum being obtained by performing Fourier transformation on the time-course data; and a power ratio comparison judgment means for comparing the ratio and a predetermined threshold value with each other, wherein when the ratio is higher than the predetermined threshold value, the power ratio comparison judgment means judges that a position shift of the sample material with respect to the sample table is present and outputs the result of the judgment.

13. An apparatus for judging a position shift, as defined in claim 3, wherein the time-course data is a moving average of the values obtained by measuring, in time series, a change in the density of each of the plurality of sample materials by a color reaction thereof.

14. An apparatus for judging a position shift, as defined in claim 4, wherein the time-course data is a moving average of the values obtained by measuring, in time series, a change in the density of each of the plurality of sample materials by a color reaction thereof.

15. An apparatus for judging a position shift, as defined in claim 5, wherein the time-course data is a moving average of the values obtained by measuring, in time series, a change in the density of each of the plurality of sample materials by a color reaction thereof.

16. An apparatus for judging a position shift, as defined in claim 6, wherein the time-course data is a moving average of the values obtained by measuring, in time series, a change in the density of each of the plurality of sample materials by a color reaction thereof.

* * * * *